US006433001B1

(12) United States Patent
Bach et al.

(10) Patent No.: US 6,433,001 B1
(45) Date of Patent: *Aug. 13, 2002

(54) 1H-INDOLE-3-GLYOXYLAMIDE SPLA$_2$ INHIBITORS

(75) Inventors: Nicholas J. Bach, Indianapolis; Robert D. Dillard, Zionsville; Susan E. Draheim, Indianapolis, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/714,364

(22) Filed: Nov. 16, 2000

Related U.S. Application Data

(60) Continuation of application No. 09/258,680, filed on Feb. 26, 1999, now Pat. No. 6,175,021, which is a continuation of application No. 08/856,271, filed on May 14, 1997, now Pat. No. 5,919,810, which is a continuation of application No. 08/469,954, filed on Jun. 6, 1995, now Pat. No. 5,654,326, which is a division of application No. 08/221,916, filed on Apr. 1, 1994, now abandoned.

(51) Int. Cl.$^7$ ........................ A61K 31/40; C07D 209/12
(52) U.S. Cl. ........................................ 514/419; 548/493
(58) Field of Search ........................... 548/493; 514/419

(56) References Cited

U.S. PATENT DOCUMENTS

| | | | |
|---|---|---|---|
| 2,825,743 A | 3/1958 | Speeter | 260/319 |
| 3,242,163 A | 3/1966 | Sarett et al. | 260/211 |
| 3,259,622 A | 7/1966 | Shen et al. | 260/247.5 |
| 3,351,630 A | 11/1967 | Shen | 260/326.12 |
| 3,449,363 A | 6/1969 | Littel | 260/326.13 |
| 3,624,103 A | 11/1971 | DeMartilis et al. | 2560/326.13 A |
| 3,691,194 A | 9/1972 | Papanastassion | 260/326.13 R |
| 3,801,594 A | 4/1974 | Poletto | 260/326.15 |
| 4,012,513 A | 3/1977 | Birchall et al. | 424/251 |
| 4,397,850 A | 8/1983 | Madelson | 424/248.4 |
| 4,552,876 A | 11/1985 | Jones et al. | |
| 5,334,719 A | 8/1994 | Frenette | |
| 5,420,289 A | 5/1995 | Musser et al. | |
| 5,639,780 A | 6/1997 | Lau et al. | |
| 5,654,326 A | 8/1997 | Bach et al. | |
| 5,733,923 A | 3/1998 | Bach et al. | |
| 5,919,943 A | 7/1999 | Bach et al. | |
| 6,175,021 B1 * | 1/2001 | Bach et al. | 548/493 |
| 6,274,616 B1 * | 8/2001 | Denney et al. | 514/419 |

FOREIGN PATENT DOCUMENTS

| | | |
|---|---|---|
| EP | 0 419 049 | 8/1990 |
| EP | 490263 A | 6/1992 |
| EP | 620214 A | 10/1994 |
| EP | 620215 A | 10/1994 |
| EP | 0675110 A1 | 3/1995 |
| WO | WO88/06885 | 9/1988 |
| WO | WO 91/06537 | 5/1991 |
| WO | WO 97/21703 | 6/1997 |
| WO | WO 97/21704 | 6/1997 |

OTHER PUBLICATIONS

Julia, Marc; Igolen, Jean; and Igolen, Hanne; Recherches en serie indolique. VI Sur quelques tryptamines substitutees *Bul. Soc. Chem., France*, 1962, pp. 1060–1068.

Romeo, E., "2–Aryl–3–Indoleglyoxylamides (FGIN–1): A New Class of Potent and Specific Ligands for the Mitochondiral DBI Receptor (MDR)", *The Journal of Pharmacology and Experimental Therapeutics*, vol. 262, No. 3, pp. 971–978 (1992).

Chemical Abstracts, vol. 67, 73028h, 1967, "Fragmentation of N–benzylindoles in Mass Spectrometry".

Alemany, A; Alvarez, E.; Lopez, O. And Herraez, M.E.; No. 565—"Inhibiteurs d'enzymes. XII—Preparation de (propargyamino–2–ethyl)–3–indoles"; *Bulletin Do La Societe 'Chimique De France*, 1974, No. 12, pp. 2883–2888.

Kollenz, Gert; Labes, Christa; "Indol–Umlagerung von 1–Diphenyl amino–2,3–dihydro–2,3–pyrrolidionen"; *Liebigs Ann. Chem.*,1975, pp. 1979–1983.

Kreft, A.; Nelson, J. Et al.; "Structure–activity relationships leading to WY–121,520 a tris aryl type, Nidomethacin–based, phospholipase A2 (PLA2)/leukotriene biosynthesis inhibitos", Issue vol. 39 (1993), pp. C33–C35, ISSN 0065–4299; publ. By Birkhauser Verlag, Basel Switzerland; (Proceeding of the Sixth International Research Assoc., Sep. 20–24, 1992 at White Haven, PA/USA, Ed., D.W. Morgan and A.K. Welton.

Seilhamer, Jeffery, et al., "Cloning and Recombinant Expression of Phospholipase A2 present in Rheumatoid Arthritic Synovial Fluid"; *The Journal of Biological Chemistry*, 254:10, Apr. 5, 1989, pp. 5335–5338.

Kramer, Ruther et al., "Structure and Properties of a Human Non–Pancreatic Phospholipase A2", *The Journal of Biological Chemistry*, 264:10, Apr. 5, 1989, pp. 5768–5775.

Reynolds, et al., "Analysis of Human Synovial Fluid Phospholipase A2 on Short Chain Phosphatidylcholine–Mixed Micelles: Development of a Spectrophotometric Assay Suitable for a Microtiterplate Reader", Analytical Biochem, 204, pp. 190–197, 1992.

Rossum, et al., "Cumulative Dose–Response Curves II. Technique for the making of dose response curves in isolated organs and the evaluation of drug parameters," Arch. Int. Pharmacodyn. 143, No. 34, pp. 299–330, 1963.

Wald, Douglas R., "Analysis of Dose–Response Relationships", Dept. Of Pharma., Univ. Of Mass. Med. Center, 145–179 (no date available).

Andreani, A., et al., "Nonsteroidal Antiinflammatory Agents. 2. Synthesis and Biological Activity of 2–Chlorindolecarboxylic Acids"; *Journal of Medicinal Chemistry*, vol. 20, No. 10, 1977, pp. 1344–1346.

(List continued on next page.)

Primary Examiner—Deborah C. Lambkin
(74) Attorney, Agent, or Firm—Roger S. Benjamin

(57) ABSTRACT

A class of novel 1H-indole-3-glyoxylamides is disclosed together with the use of such indole compounds for inhibiting sPLA2 mediated release of fatty acids for treatment of conditions such as septic shock.

1 Claim, No Drawings

OTHER PUBLICATIONS

Julia, Marc., et al., "No. 208—Recherches en series indolique. XIII. Sur quelques methoxy −5 et. −6 tryptamines", *Bulletin de La Societe Chemique de France*, Paris France; 1965, pp. 1411–1417.

Chemical Abstracts, vol. 1/2 No. 24, Abstract No. 223181s; "Kinetics of hydrolysis of indomethacin and indomethacin ester predrugs in aqueous solution" Jun. 11, 1990, p. 407.

Chemical Abstracts Service. "Registry Handbook", Number Section, Registry Numbers (see, CAS RN 6264–33–1) 1965–1971, Publ. American Chemical Society.

Von K.H. Boltze; O. Brendler, et al., "Chemische Struktur and antiphlogistische Wirkung in der Reihe der substituierten Indol–3–essigsauren," *Arznermittel Forschung Drug Research*, vol. 30 (II), No. 8A, 1980, Aluendorf, DE, pp. 1314–1325.

Dillard, Robert D., et al., Indole Inhibitors of Human Non-pancreatic Secretory Phospholipase A2–1. Indole–3–acetamides, *Journal of Medicinal Chemistry*, vol. 39, No. 26, pp. 5119–5136.

Dillard, Robert D., et al., Indole Inhibitors of Human Non-pancreatic Secretory Phospholipase A2–2. Indole–3–acetamides with Additional Functionality, *Journal of Medicinal Chemistry*, vol. 39, No. 26, pp. 5137–5158.

Draheim, Susan E., et al., Indole Inhibitors of Human Nonpancreatic Secretory Phospholipase A2–3. Indole–3–glyoxamides, *Journal of Medicinal Chemistry*, vol. 39, No. 26, pp. 5159–5175.

* cited by examiner

1H-INDOLE-3-GLYOXYLAMIDE SPLA$_2$ INHIBITORS

This application is a continuation of Ser. No. 09/258,680 filed Feb. 26, 1999, U.S. Pat. No. 6,175,021 which is a continuation of Ser. No. 08/856,271 filed May 14, 1997, U.S. Pat. No. 5,919,810, which is a continuation of Ser. No. 08/469,954 filed Jun. 6, 1995, U.S. Pat. No. 5,654,326, which is a divisional of Ser. No. 08/221,916 filed Apr. 1, 1994, abandoned.

BACKGROUND OF THE INVENTION

1. Field of the Invention

This invention relates to novel 1H-indole-3-glyoxylamides useful for inhibiting sPLA$_2$ mediated release of fatty acids, for conditions such as septic shock.

2. Background Information

The structure and physical properties of human non-pancreatic secretory phospholipase A$_2$ (hereinafter called, "sPLA$_2$") has been thoroughly described in two articles, namely, "Cloning and Recombinant Expression of Phospholipase A$_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of April 5, pp. 5335–5338, 1989; and "Structure and Properties of a Human Non-pancreatic Phospholipase A$_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of April 5, pp. 5768–5775, 1989; the disclosures of which are incorporated herein by reference.

It is believed that sPLA$_2$ is a rate limiting enzyme in the arachidonic acid cascade which hydrolyzes membrane phospholipids. Thus, it is important to develop compounds which inhibit sPLA$_2$ mediated release of fatty acids (e.g., arachidonic acid). Such compounds would be of value in general treatment of conditions induced and/or maintained by overproduction of sPLA$_2$; such as septic shock, adult respiratory distress syndrome, pancreatitis, trauma, bronchial asthma, allergic rhinitis, rheumatoid arthritis, and etc.

The article, "Recherches en serie indolique. VI sur tryptamines substituees", by Marc Julia, Jean Igolen and Hanne Igolen, *Bull. Soc. Chim. France*, 1962, pp. 1060–1068, describes certain indole-3-glyoxylamides and their conversion to tryptamine derivatives.

The article, "2-Aryl-3-Indoleglyoxylamides (FGIN-1): A New Class of Potent and Specific Ligands for the Mitochondrial DBI Receptor (MDR)" by E. Romeo, et al., *The Journal of Pharmacology and Experimental Therapeutics*, Vol. 262, No. 3, (pp. 971–978) describes certain 2-aryl-3-indolglyoxylamides having research applications in mammalian central nervous systems.

The abstract, "Fragmentation of N-benzylindoles in Mass Spectrometry"; Chemical Abstracts, Vol. 67, 1967, 73028h, reports various benzyl substituted phenols including those having glyoxylamide groups at the 3 position of the indole nucleus.

European Patent 490263 discloses oxoacetamide derivatives of indoles having serotonin receptor activity.

U.S. Pat. No. 3,449,363 describes trifluoromethylindoles having glyoxylamide groups at the 3 position of the indole nucleus. These compounds are stated to be analgesics in antagonizing phenyl-p-quinone "writhing syndrome."

U.S. Pat. No. 3,351,630 describes alpha-substituted 3-indolyl acetic acid compounds and their preparation inclusive of glyoxylamide intermediates.

U.S. Pat. No. 2,825,734 describes the preparation of 3-(2-amino-1-hydroxyethyl) indoles using 3-indole glyoxylamide intermediates such as 1-phenethyl-2-ethyl-6-carboxy-N-propyl-3-indoleglyoxylamide (see, Example 30).

U.S. Pat. No. 4,397,850 prepares isoxazolyl indolamines using glyoxylamide indoles as intermediates.

U.S. Pat. No. 3,801,594 describes analgesics prepared using 3-indole glyoxylamide intermediates.

The article, "No. 565.—Inhibiteurs d'enzymes. XII.—Preparation de (propargyamino-2 ethyl)-3 indoles" by A. Alemanhy, E. Fernandez Alvarez, O. Nieto Lopey and M. E. Rubio Herraez; *Bulletin Do La Societe Chimiqque De France*, 1974, No. 12, pgs. 2883–12888 describes various indolyl-3 glyoxamides which are hydrogen substituted on the 6 membered ring of the indole nucleus.

The article "Indol-Umlagerung von 1-Diphenylamino-2, 3-dihydro-2,3-pyirroldionen" by Gert Kollenz and Christa Labes; *Liebigs Ann. Chem.*, 1975, pgs. 1979–1983 describes phenyl substituted 3-glyoxylamides.

It is desirable to develop new compounds and treatments for sPLA$_2$ induced diseases.

SUMMARY OF THE INVENTION

This invention is a novel use of the class of compounds known as 1H-indole-3-glyoxylamides to inhibit human sPLA$_2$ mediated release of fatty acids.

This invention is also novel classes of 1H-indole-3-glyoxylamides having potent and selective effectiveness as inhibitors of human sPLA$_2$.

This invention is also pharmaceutical compositions containing the 1H-indole-3-glyoxylamides of the invention.

This invention is also a method of preventing and treating septic shock, adult respiratory distress syndrome, panceatitus, trauma, bronchial asthma, allergic rhinitis, rheumatoid arthritis, and related diseases by contact with a therapeutically effective amount of the 1H-indole-3-glyoxylamides of the invention.

DETAILED DESCRIPTION OF THE INVENTION

Definitions

The 1H-indole-3-acetamides of the invention employ certain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, n-pentyl, and n-hexyl.

The term, "alkenyl" employed alone or in combination with other terms means a straight chain or branched monovalent hydrocarbon group having the stated number range of carbon atoms, and typified by groups such as vinyl, propenyl, crotonyl, isopentenyl, and various butenyl isomers.

The term, "hydrocarbyl" means an organic group containing only carbon and hydrogen.

The term, "halo" means fluoro, chloro, bromo, or iodo.

The term, "heterocyclic radical", refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, thianaphtheneyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pryidinyl, dipyridylyl. phenylpyridinyl, benzylpyridinyl, pyrimidinyl, phlenylpyrimidinyl, pyrazinyl, 1,3,5-triazinyl, quinolinyl, phthalazinyl, quinazolinyl, and quinoxalinyl.

The term, "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, naphthyl, norbornanyl, bicycloheptadienyl, tolulyl, xylenyl, indenyl, stilbenyl, terphenylyl, diphenylethylenyl, phenyl-cyclohexenly, acenaphthylenyl, and anthracenyl, biphenyl, bibenzylyl and related bibenzylyl homologues represented by the formula (bb),

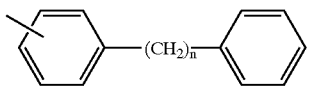

(bb)

where n is a number from 1 to 8.

The term, "non-interfering substituent", refers to radicals suitable for substitution at positions 4, 5, 6, and/or 7 on the indole nucleus (as hereinafter depicted in Formula I) and radical(s) suitable for substitution on the heterocyclic radical and carbocyclic radical as defined above. Illustrative non-interfering radicals are $C_1$–$C_6$ alkyl, $C_1$–$C_6$ alkenyl, $C_1$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_2$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —(CH$_2$)$_n$—O—($C_1$–$C_6$) alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1$–$C_6$ carbonyl; where n is from 1 to 8.

The term, "acidic group" means an organic group which when attached to an indole nucleus, through suitable linking atoms (hereinafter defined as the "acid linker"), acts as a proton donor capable of hydrogen bonding. Illustrative of an acidic group are the following:

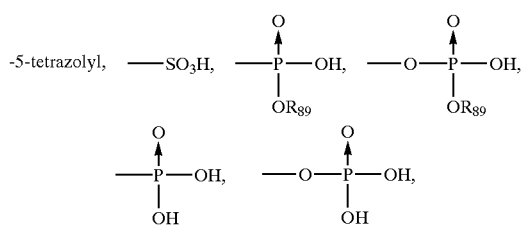

-continued

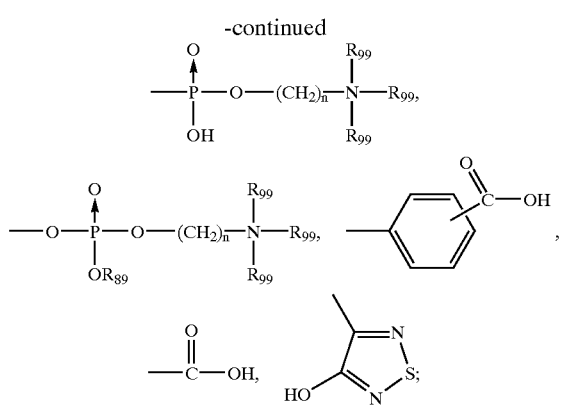

where n is 1 to 8, $R_{89}$ is a metal or $C_1$–$C_{10}$ alkyl, and $R_{99}$ is hydrogen or $C_1$–$C_{10}$ alkyl.

The words, "acid linker" refer to a divalent linking group symbolized as, —($L_a$)—, which has the function of joining the 4 or 5 position of the indole nucleus to an acidic group in the general relationship:

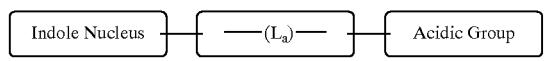

The words, "acid linker length", refer to the number of atoms (excluding hydrogen) in the shortest chain of the linking group —($L_a$)— that connects the 4 or 5 position of the indole nucleus with the acidic group. The presence of a carbocyclic ring in —($L_a$)— counts as the number of atoms approximately equivalent to the calculated diameter of the carbocyclic ring. Thus, a benzene or cyclohexane ring in the acid linker counts as 2 atoms in calculating the length of —($L_a$)—. Illustrative acid linker groups are;

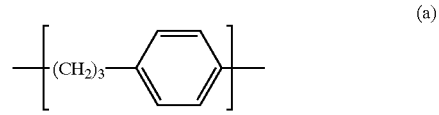

(a)

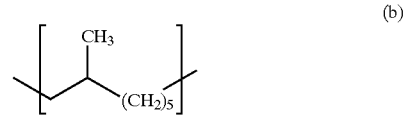

(b)

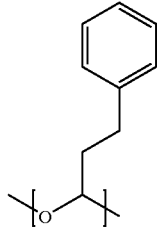

(c)

wherein, groups (a), (b), and (c) have acid linker lengths of 5, 7, and 2, respectively.

The term, "amine", includes primary, secondary and tertiary amine.

The 1H-indole-3-glyoxylamide Compounds of the Invention

The compounds of the invention have the general formula (I);

(I)

wherein;

each X is independently oxygen or sulfur;

$R_1$ is selected from groups (a), (b) and (c) where;
- (a) is $C_7$–$C_{20}$ alkyl, $C_7$–$C_{20}$ alkenyl, $C_7$–$C_{20}$ alkynyl, carbocyclic radicals, or heterocyclic radicals, or
- (b) is a member of (a) substituted with one or more independently selected non-interfering substituents; or
- (c) is the group —(L)— $R_\lambda$; where, —(L)— is a divalent linking group of 1 to 12 atoms selected from carbon, hydrogen, oxygen, nitrogen, and sulfur; wherein the combination of atoms in —(L)— are selected from the group consisting of (i) carbon and hydrogen only, (ii) sulfur only, (iii) oxygen only, (iv) nitrogen and hydrogen only, (v) carbon, hydrogen, and sulfur only, and (vi) and carbon, hydrogen, and oxygen only; and where $R_{80}$ is a group selected from (a) or (b);

$R_2$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1 to 3 atoms other than hydrogen; (that is, the $R_2$ radical may contain hydrogen atoms, but the remaining atoms comprising the total of 1 to 3 are non-hydrogen);

$R_4$ and $R_5$ are independently selected from hydrogen, a non-interfering substituent, or the group, —($L_a$)-(acidic group); wherein —(La)—, is an acid linker having an acid linker length of 1 to 4; provided, that at least one of $R_4$ and $R_5$ must be the group, —(La)-(acidic group);

$R_6$ and $R_7$ are each independently selected form hydrogen, noninterfering substituent, carbocyclic radicals, carbocyclic radicals substituted with non-interfering substituents, heterocyclic radicals, and heterocyclic radicals substituted with non-interfering substituents.

Preferred Subgroups of Compounds of Formula (I)

A preferred subclass of compounds of formula (I) are those wherein both X are oxygen.

Another preferred subclass of compounds of formula (I) are those wherein $R_2$ is selected from the group; halo, cyclopropyl, methyl, ethyl, propyl, —O-methyl, and —S-methyl.

Another preferred subclass of compounds of formula (I) are those wherein for $R_1$, —(L)— is an alkylene chain of 1 or 2 carbon atoms.

Another preferred subclass of compounds of formula (I) are those wherein for $R_1$, group $R_{80}$ is selected from the group consisting of cycloalkyl, cycloalkenyl, phenyl, naphthyl, norbornanyl, bicycloheptadienyl, tolulyl, xylenyl, indenyl, stilbenyl, teriphenylyl, diphenylethylenyl, phenyl-cyclohexenyl, acenaphthylenyl, and anthracenyl, biphenyl, bibenzylyl and related bibenzylyl homologues represented by the formula (bb), (bb)

where n is a number from 1 to 8. Particularly preferred are compounds wherein $R_1$ is selected from the group consisting of and where $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl, and t is a number from 0 to 5.

Another preferred subclass of compounds of formula (I) are those wherein $R_4$ is a substituent having an acid linker with an acid linker length of 2 or 3. Most preferred are compounds where the acidic group is selected from -5-tetrazolyl,

—$SO_3H$, where n is 1 to 8, $R_{89}$ is a metal or $C_1$–$C_{10}$ alkyl, and $R_{99}$ is hydrogen or $C_1$–$C_{10}$ alkyl. Particularly preferred are compounds wherein the acidic group of $R_4$ is selected from;

—$CO_2H$,    —$SO_3H$,    —$P(O)(OH)_2$, or salt, and prodrug (e.g., ester) derivatives thereof.

Another preferred subclass of compounds of formula (I) are those wherein $R_4$ is a substituent having an acid linker with an acid linker length of 2 or 3 and the acid linker group, —($L_a$)—, for $R_4$ is selected from a group represented by the formula;

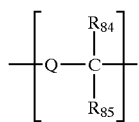

where Q is selected from the group —(CH$_2$)—, —O—, —NH—, and —S—, and R$_{84}$ and R$_{85}$ are each independently selected from hydrogen, C$_1$–C$_{10}$ alkyl, aryl, C$_1$–C$_{10}$ alkaryl, C$_1$–C$_{10}$ aralkyl, carboxy, carbalkoxy, and halo. Most preferred are compounds where the acid linker, —(L$_a$)—, for R$_4$ is selected from the specific group;,

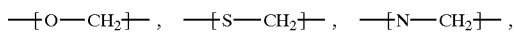

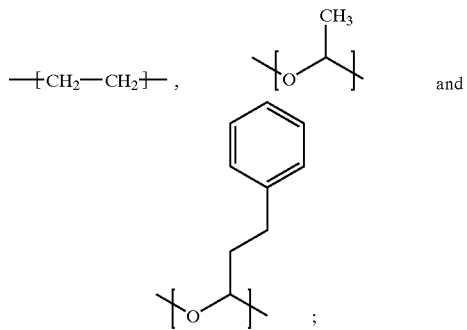

Another preferred subclass of compounds of formula (I) are those wherein R$_5$ is a substituent having an acid linker with an acid linker length of 3 to 8 atoms. Most preferred are compounds where the acidic group is selected from -5-tetrazolyl,

—SO$_3$H,

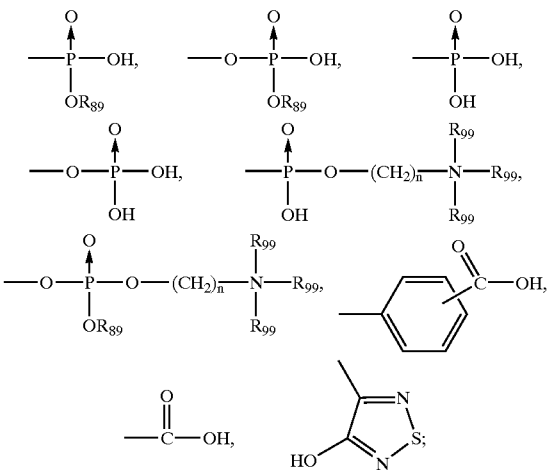

where n is 1 to 8, R$_{89}$ is a metal or C$_1$–C$_{10}$ alkyl, and R$_{99}$ is hydrogen or C$_1$–C$_{10}$ alkyl. Particularly preferred are compounds wherein the acidic group of R$_4$ is selected from;

or salt, and prodrug (e.g., ester) derivatives thereof.

Another preferred subclass of compounds of formula (I) are those wherein R$_5$ is a substituent having an acid linker with an acid linker length of 3 to 8 atoms and the acid linker group, —(L$_a$)—, for R$_5$ is selected from;

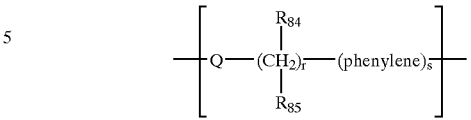

where r is a number from 2 to 7, s is 0 or 1, and Q is selected from the group —(CH$_2$)—, —O—, —NH—, and —S—, and R$_{84}$ and R$_{85}$ are each independently selected from hydrogen, C$_1$–C$_{10}$ alkyl, aryl, C$_1$–C$_{10}$ alkaryl, C$_1$–C$_{10}$ aralkyl, carboxy, carbalkoxy, arid halo. Most preferred are compounds where the acid linker, —(L$_a$)—, for R$_5$ is selected from the specific groups;

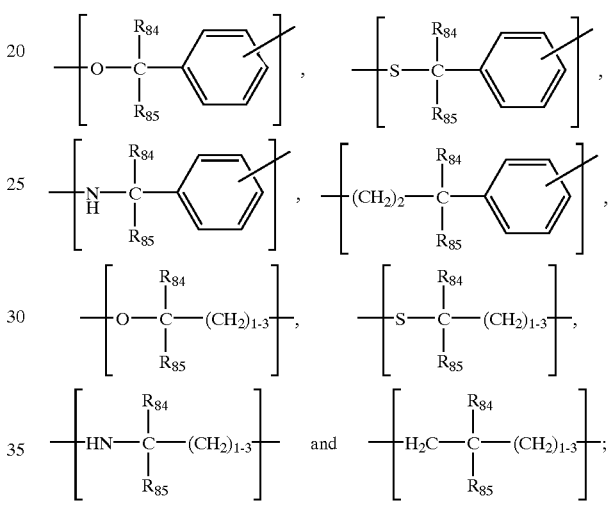

wherein R$_{84}$ and R$_{85}$ are each independently selected from hydrogen, C$_1$–C$_{10}$ alkyl, aryl, C$_1$–C$_{10}$ alkaryl, C$_1$–C$_{10}$ aralkyl, carboxy carbalkoxy, and halo.

Another preferred subclass of compounds of formula (I) are those wherein R$_6$, and R$_7$ are each independently selected from hydrogen and non-interfering substituents, with the non-interfering substituents being selected from the group consisting of C$_1$–C$_6$ alkyl, C$_1$–C$_6$ alkenyl, C$_1$–C$_6$ alkynyl, C$_7$–C$_{12}$ aralkyl, C$_7$–C$_{12}$ alkaryl, C$_3$–C$_8$ cycloalkyl, C$_3$–C$_8$ cycloalkenyl, phenyl, tolulyl, xylenyl, biphenyl, C$_1$–C$_6$ alkoxy, C$_1$–C$_6$ alkenyloxy, C$_1$–C$_6$ alkynyloxy, C$_2$–C$_{12}$ alkoxyalkyl, C$_2$–C$_{12}$ alkoxyalkyloxy, C$_2$–C$_{12}$ alkylcarbonyl, C$_2$–C$_{12}$ alkylcarbonylamino, C$_2$–C$_{12}$ alkoxyamino, C$_2$–C$_{12}$ alkoxyaminocarbonyl, C$_2$–C$_{12}$ alkylamino, C$_1$–C$_6$ alkylthio, C$_2$–C$_{12}$ alkylthiocarbonyl, C$_1$–C$_6$ alkylsulfinyl, C$_1$–C$_6$ alkylsulfonyl, C$_2$–C$_6$ haloalkoxy, C$_1$–C$_6$ haloalkylsulfonyl, C$_2$–C$_6$ haloalkyl, C$_1$–C$_6$ hydroxyalkyl, —C(O)O(C$_1$–C$_6$ alkyl), —(CH$_2$)$_n$—O—(C$_1$–C$_6$ alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and C$_1$–C$_6$ carbonyl; where n is from 1 to 8.

Preferred compounds of the invention are those having the general formula (II);

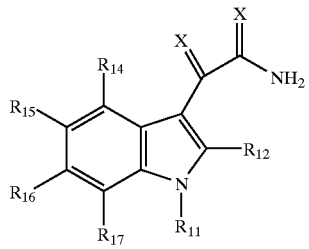

(II)

wherein;
each X is independently oxygen or sulfur;
$R_{11}$ is selected from groups (a), (b) and (c) where;
(a) is $C_7-C_{20}$ alkyl, $C_7-C_{20}$ alkenyl, $C_7-C_{20}$ alkynyl; or a carbocyclic radical selected from the group cycloalkyl, cycloalkenyl, phenyl, naphthyl, norbornanyl, bicycloheptadienyl, tolulyl, xylenyl, indenyl, stilbenyl, terphenylyl, diphenylethylenyl, phenyl-cyclohexenyl, acenaphthylenyl, and anthracenyl, biphenyl, bibenzylyl and related bibenizylyl homologues represented by the formula (bb),

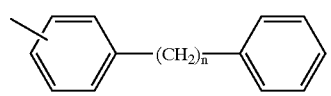

(bb)

where n is a number from 1 to 8; or
(b) is a member of (a) substituted with one or more independently selected non-interfering substituents selected from the group consisting of $C_1-C_6$ alkyl, $C_1-C_6$ alkenyl, $C_1-C_6$ alkynyl, $C_7-C_{12}$ aralkyl, $C_7-C_{12}$ alkaryl, $C_3-C_8$ cycloalkyl, $C_3-C_8$ cycloalkenyl, phenyl, tolulyl, xylenyl, biphenyl, $C_1-C_6$ alkoxy, $C_1-C_6$ alkenyloxy, $C_1-C_6$ alkynyloxy, $C_2-C_{12}$ alkoxyalkyl, $(C_2-C_{12}$ alkoxyalkyloxy, $C_2-C_{12}$ alkylcarbonyl, $C_2-C_{12}$ alkylcarbonylamino, $C_2-C_{12}$ alkoxyamino, $C_2-C_{12}$ alkoxyaminocalbonyl, $C_2-C_{12}$ alkylamino, $C_1-C_6$ alkylthio, $C_2-C_{12}$ alkylthiocarbonyl, $C_1-C_6$ alkylsulfinyl, $C_1-C_6$ alkylsulfonyl, $C_2-C_6$ haloalkoxy, $C_1-C_6$ haloalkylsulfonyl, $C_2-C_6$ haloalkyl, $C_1-C_6$ hydroxyalkyl, $—C(O)O(C_1-C_6$ alkyl), $—(CH_2)_n—O—(C_1-C_6$ alkyl), benzyloxy, phenoxy, phenylthio, $(—CONHSO_2R)$, —CHO, amino, amidino, bromo, carbamyl, carboxyl, carbalkoxy, $—(CH_2)_n—CO_2H$, chloro, cyano, cyanoguanidinyl, fluoro, guanidino, hydrazide, hydrazino, hydrazido, hydroxy, hydroxyamino, iodo, nitro, phosphono, $—SO_3H$, thioacetal, thiocarbonyl, and $C_1-C_6$ carbonyl; where n is from 1 to 8; or
(c) is the group $—(L_1)—R_{81}$; where, $—(L_1)—$ is a divalent linking group having the formula;

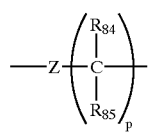

where,
$R_{84}$ and $R_{85}$ are each independently selected from hydrogen, $C_1-C_{10}$ alkyl, aryl, $C_1-C_{10}$ alkaryl, $C_1-C_{10}$ aralkyl, carboxy, carbalkoxy, and halo;

p is 1 to 5,
Z is a bond, $—(CH_2)—$, $—O—$, $—N(C_1-C_{10}$ alkyl)—, —NH—, or —S—; and
where $R_{81}$ is a group selected from (a) or (b);
$R_{12}$ is hydrogen, halo, $C_1-C_3$ alkyl, $C_3-C_4$ cycloalkyl, $C_3-C_4$ cycloalkenyl, $—O—(C_1-C_2$ alkyl), or $—S—(C_1-C_2$ alkyl);
$R_{14}$ is selected from hydrogen, a non-interfering substituent, or the group, $—(La)$-(acidic group), wherein the acid linker $—(La)—$ has an acid linker length of 2 or 3 atoms and is represented by the formula;

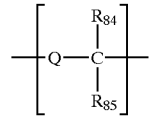

where Q is selected from the group $—(CH_2)—$, $—O—$, —NH—, and —S—; $R_{84}$ and $R_{85}$ are each independently selected from hydrogen, $C_1-C_{10}$ alkyl, aryl, $C_1-C_{10}$ alkaryl, $C_1-C_{10}$ aralkyl, hydroxy, and halo; and the acidic group is selected from -5-tetrazolyl, $—SO_3H$,

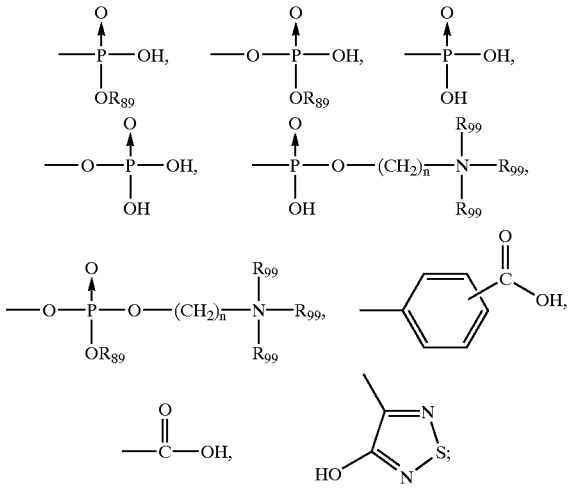

where n is 1 to 8, $R_{89}$ is a metal or $C_1-C_{10}$ alkyl, and $R_{99}$ is hydrogen or $C_1-C_{10}$ alkyl;
$R_{15}$ is selected from hydrogen, a non-interfering substituent, or the group, $—(L_a)$-(acidic group), wherein the acid linker $—(L_a)—$ has an acid linker length of 3 to 8 atoms and the acid linker group, $—(L_a)—$ is;

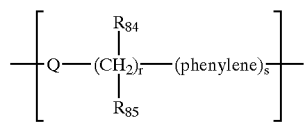

where r is a number from 2 to 7, s is 0 or 1, and Q is selected from the group $—(CH_2)—$, $—O—$, —NH—, and —S—; and $R_{84}$ and $R_{85}$ are each independently selected from hydrogen, $C_1-C_{10}$ alkyl, aryl, $C_1$–$C_{10}$ alkaryl, $C_1$–$C_{10}$ aralkyl, carboxy, carbalkoxy, and halo; and the acidic group is selected from -5-tetrazolyl,

—$SO_3H$,

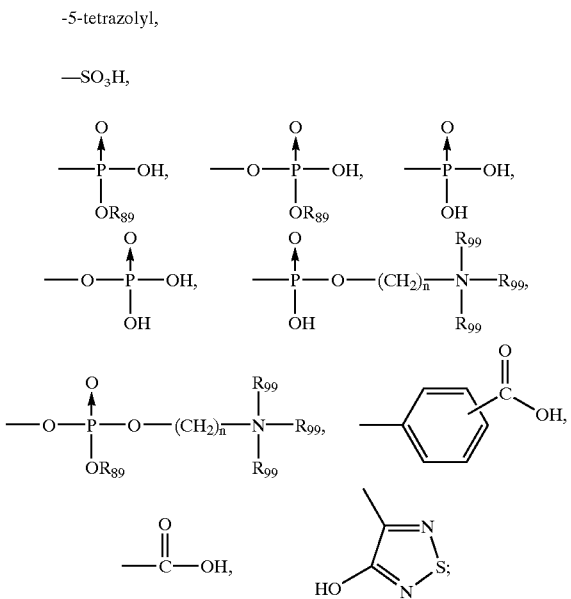

where n is 1 to 8, $R_{89}$ is a metal or $C_1$–$C_{10}$ alkyl, and $R_{99}$ is hydrogen or $C_1$–$C_{10}$ alkyl;

provided that at least one of $R_{14}$ or $R_{15}$ must be the group, —($L_a$)-(acidic group);

$R_{16}$, and $R_{17}$ are each independently selected form hydrogen, non-interfering substituents, selected from the group consisting of $C_1$–$C_6$ alkyl, $C_1$–$C_6$ alkenyl, $C_1$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_2$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —($CH_2$)$_n$—O—($C_1$–$C_6$ alkyl), benzyloxy, phenoxy, phenylthio, —($CONHSO_2R$), —CHO, amino, amidino, bromo, carbamyl, carboxyl, carbalkoxy, —($CH_2$)$_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$–$C_6$ carbonyl; where n is from 1 to 8.

A preferred class of compounds according to this invention are the compounds represented by the formula (II) where X is oxygen.

Another preferred class of compounds according to this invention are the compounds represented by formula (II) where the acid linker, —($L_a$)—, for $R_{15}$ is selected from the groups;

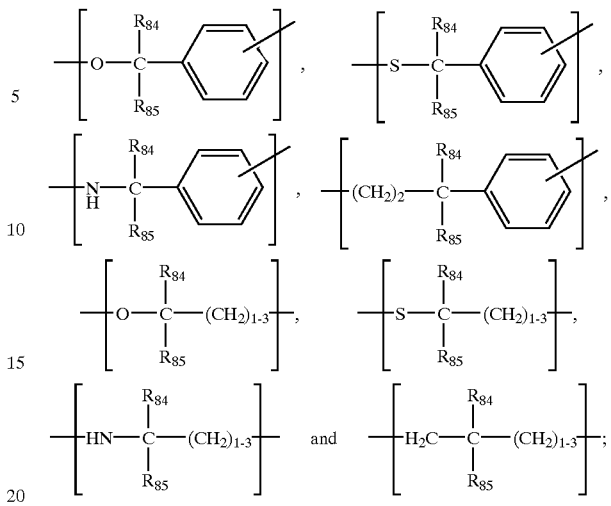

wherein $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo;

Specific preferred compounds and all pharmaceutically acceptable salts, solvates and prodrug derivatives thereof which are illustrative of the compounds of the invention include the following:

(A) [[3-(2-Amino-1,2-dioxoethyl)-2-methyl-1-(phenylmethyl)-1H-indol-4-yl]oxy]acetic acid,
(B) dl-2-[[3-(2-Amino-1,2-dioxoethyl)-2-methyl-1-(phenylmethyl)-1H-indol-4-yl]oxy]propanoic acid,
(C) [[3-(2-Amino-1,2-dioxoethyl)-1-([1,1'-biphenyl]-2-ylmethyl)-2-methyl-1H-indol-4-yl]oxy]acetic acid,
(D) [[3-(2-Amino-1,2-dioxoethyl)-1-([1,1'-biphenyl]-3-ylmethyl)-2-methyl-1H-indol-4-yl]oxy]acetic acid,
(E) [[3-(2-Amino-1,2-dioxoethyl)-1-([1,1'-biphenyl]-4-ylmethyl)-2-methyl-1H-indol-4-yl]oxy]acetic acid,
(F) [[3-(2-Amino-1,2-dioxoethyl)-1-[(2,6-dichlorophenyl)methyl]-2-methyl-1H-indol-4-yl]oxy]acetic acid
(G) [[3-(2-Amino-1,2-dioxoethyl)-1-[4(-fluorophenyl)methyl]-2-methyl-1H-indol-4-yl]oxy]acetic acid,
(H) [[3-(2-Amino-1,2-dioxoethyl)-2-methyl-1-[(1-naphthalenyl)methyl]-1H-indol-4-yl]oxy]acetic acid,
(I) [[3-(2-Amino-1,2-dioxoethyl)-2-ethyl-1-(phenylmethyl)-1H-indol-4-yl]oxy]acetic acid,
(J) [[3-(2-Amino-1,2-dioxoethyl)-1-[(3-chlorophenyl)methyl]-2-ethyl-1H-indol-4-yl]oxy]acetic acid,
(K) [[3-(2-Amino-1,2-dioxoethyl)-1-([1,1'-biphenyl]-2-ylmethyl)-2-ethyl-1H-indol-4-yl]oxy]acetic acid,
(L) [[3-(2-amino-1,2-dioxoethyl)-1-([1,1'-biphenyl]-2-ylmethyl)-2-propyl-1H-indol-4-yl]oxy]acetic acid,
(M) [[3-(2-Amino-1,2-dioxoethyl)-2-cyclopropyl-1-(phenylmethyl)-1H-indol-4-yl]oxy]acetic acid,
(N) [[3-(2-Amino-1,2-dioxoethyl)-1-([1,1'-biphenyl]-2-ylmethyl)-2-cyclopropyl-1H-indol-4-yl]oxy]acetic acid,
(O) 4-[[3-(2-Amino-1,2-dioxoethyl)-2-ethyl-1-(phenylmethyl )-1H-indol-5-yl]oxy]butanoic acid, and
(P) mixtures of (A) thru (O) in any combination.

The salts of the above 1H-indole-3-glyoxylamide compounds represented by formulae (I) and (II) and named compounds (A) thru (P) are an additional aspect of the invention. In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.,* 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethlane sulfonate, and valerate.

Certain compounds of the invention may possess one or more chiral centers and may thus exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs,* pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy)alkyl esters or ((alkoxycarbonyl)oxy)alkyl esters.

Synthesis Methods

The synthesis of the 1H-indole-3-glyoxylamides of structure 1 can be accomplished by known methods. Procedures useful for the syntheses of the compounds of this invention are outlined in the following reaction schemes:

The synthesis of the 1H-indole-3-glyoxylamides of structure I clan be accomplished by well known methods as recorded in the chemical literature. Those procedures useful for the syntheses of the compounds of the invention are illustrated herein and outlined in the following reaction schemes 1 through 8.

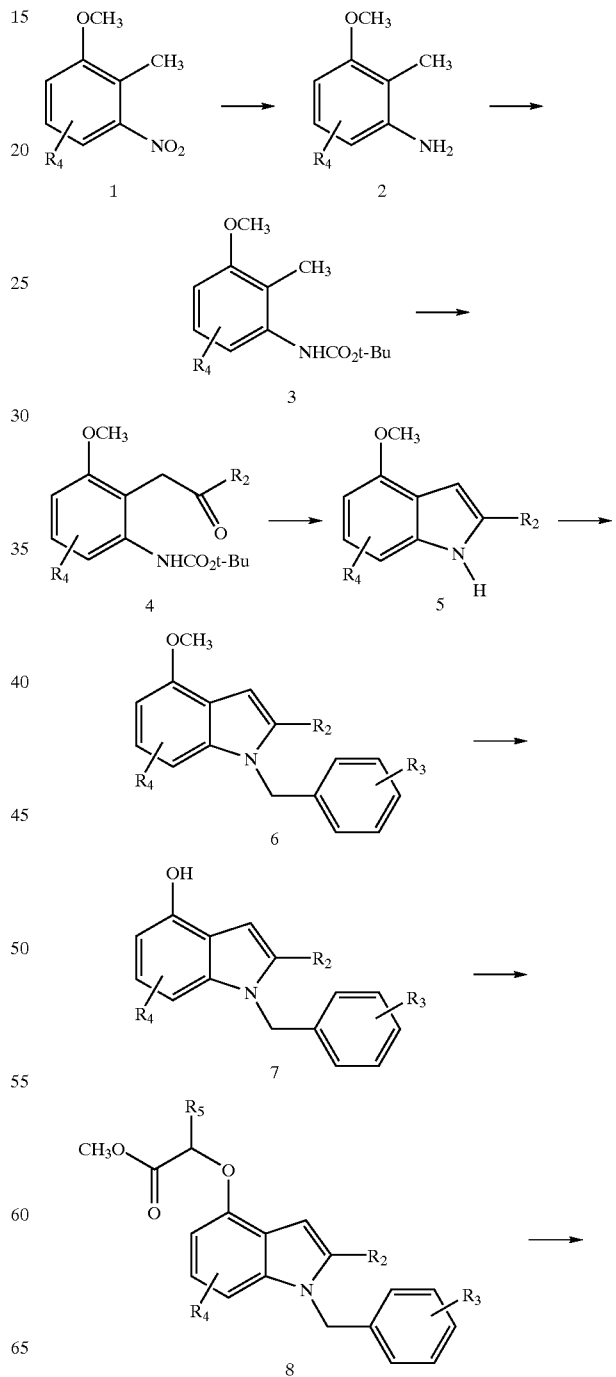

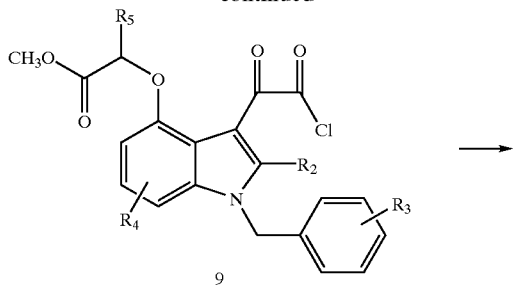

9

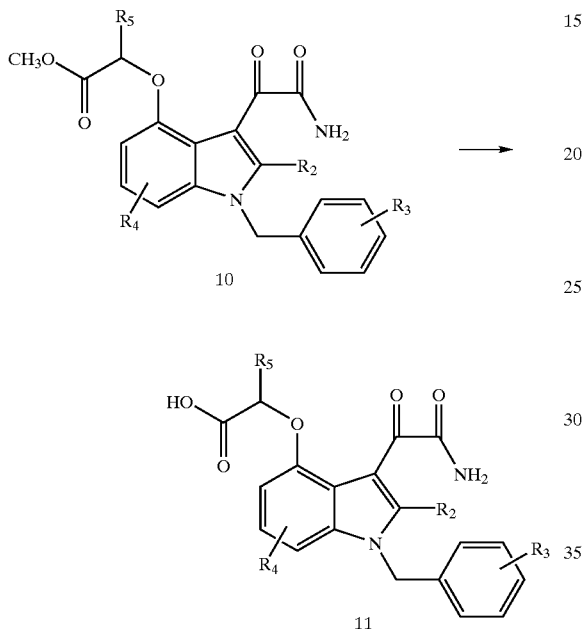

10

11

To obtain the glyoxylamides substituted in the 4-position with an acidic function through an oxygen atom, the reactions outlined in scheme 1 are used (for conversions 1 thru 5, see ref. Robin D. Clark, Joseph M. Muchowski, Lawrence E. Fisher, Lee A. Flippin, David B. Repke, Michel Souchet, *Synthesis,* 1991, 871–878, the disclosures of which are incorporated herein by reference). The ortho-nitrotoluene, 1, is readily reduced to the 2-methylaniline, 2, using Pd/C as catalyst. The reduction can be carried out in ethanol or tetrahydrofuran (THF) or a combination of both, using a low pressure of hydrogen. The aniline, 2, on heating with di-tert-butyl dicarbonate in THF at reflux temperature is converted to the N-tert-butylcarbonyl derivative, 3, in good yield. The dilithium salt of the dianion of 3 is generated at –40 to –20° C. in THF using sec-butyl lithium and reacted with the appropriately substituted N-methoxy-N-methylalkanamide. This product, 4, may be purified by crystallization from hexane, or reacted directly with trifluoroacetic acid in methylene chloride to give the 1,3-unsubstituted indole 5. The 1,3-unsubstituted indole 5 is reacted with sodium hydride in dimethylformamide at room temperature (20–25° C.) for 0.5–1.0 hour. The resulting sodium salt of 5 is treated with an equivalent of arylmethyl halide and the mixture stirred at a temperature range of 0–100° C., usually at ambient room temperature, for a period of 4 to 36 hours to give the 1-arylmethylindole, 6. This indole, 6, is O-demethylated by stirring with boron tribromide in methylene chloride for approximately 5 hours (see ref. Tsung-Ying Shem and Charles A Winter, *Adv. Drug Res.,* 1977, 12, 176, the disclosure of which is incorporated herein by reference). The 4-hydroxyindole, 7, is alkylated with an alpha bromoalikanoic acid ester in dimethylformamide (DMF) using sodium hydride as a base, with reactions conditions similar to that described for the conversion of 5 to 6. The α-[(indol-4-yl)oxy]alkanoic acid ester, 8, is reacted with oxalyl chloride in methylene chloride to give 9, which is not purified but reacted directly with ammonia to give the glyoxamide 10. This product is hydrolyzed using 1N sodium hydroxide in MeOH. The final glyoxylamide, 11, is isolated either as the free carboxylic acid or as its sodium salt or in both forms.

Scheme 2

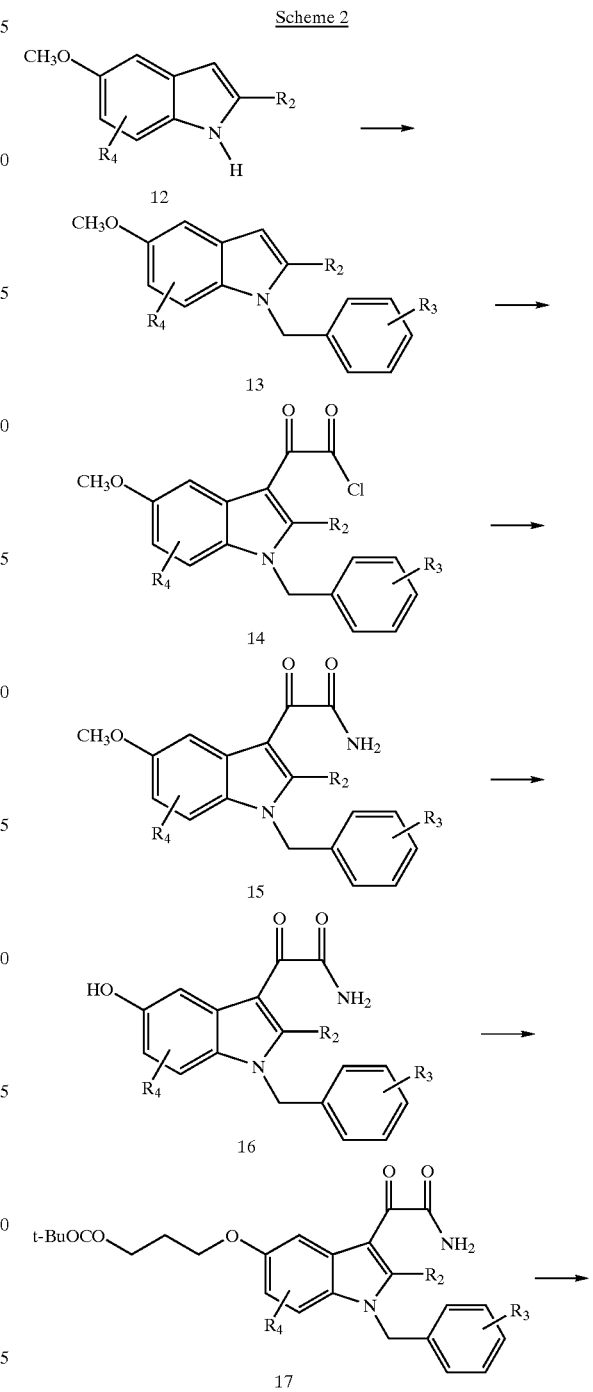

17
-continued

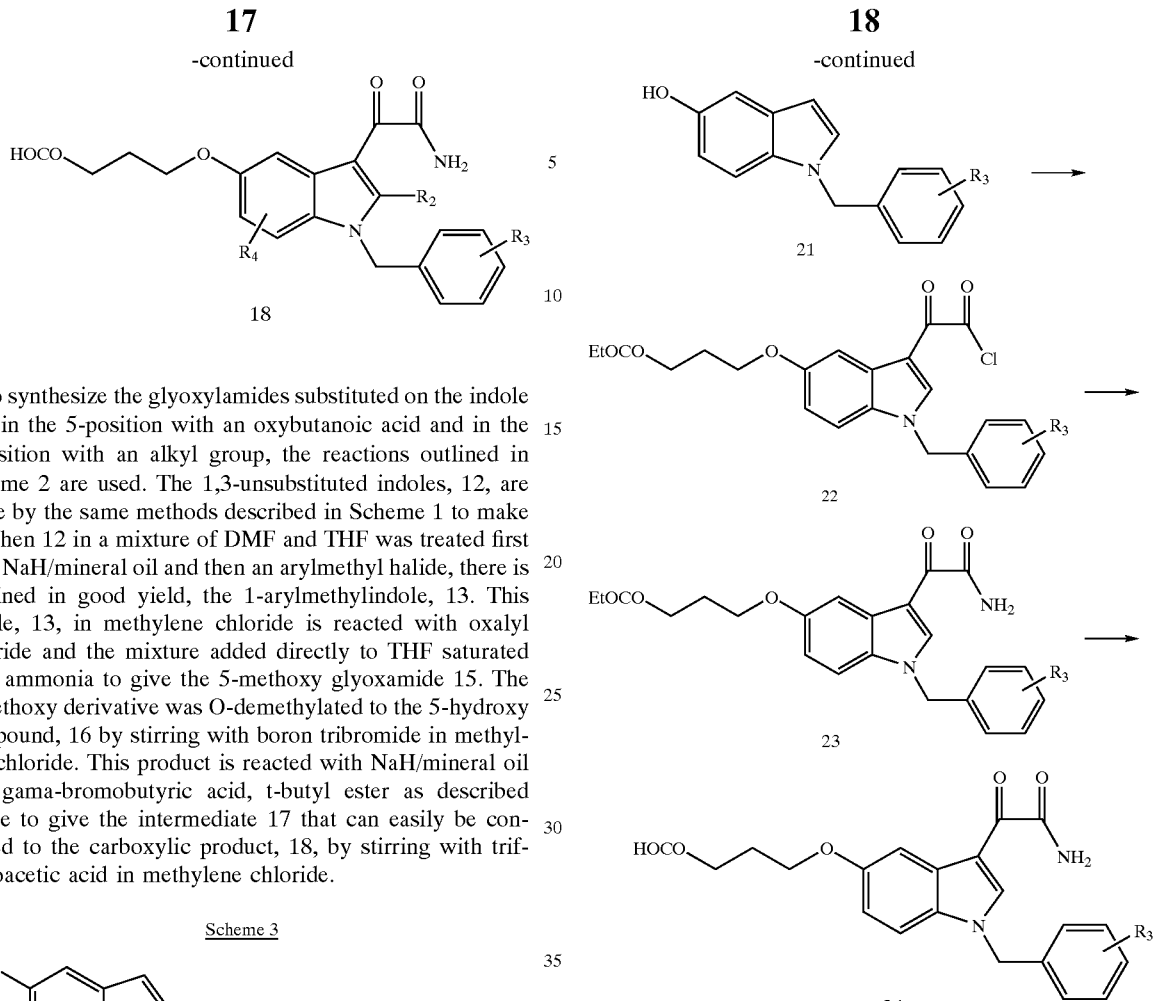

To synthesize the glyoxylamides substituted on the indole ring in the 5-position with an oxybutanoic acid and in the 2-position with an alkyl group, the reactions outlined in Scheme 2 are used. The 1,3-unsubstituted indoles, 12, are made by the same methods described in Scheme 1 to make 5. When 12 in a mixture of DMF and THF was treated first with NaH/mineral oil and then an arylmethyl halide, there is obtained in good yield, the 1-arylmethylindole, 13. This indole, 13, in methylene chloride is reacted with oxalyl chloride and the mixture added directly to THF saturated with ammonia to give the 5-methoxy glyoxamide 15. The 5-methoxy derivative was O-demethylated to the 5-hydroxy compound, 16 by stirring with boron tribromide in methylene chloride. This product is reacted with NaH/mineral oil and gama-bromobutyric acid, t-butyl ester as described above to give the intermediate 17 that can easily be converted to the carboxylic product, 18, by stirring with trifluoroacetic acid in methylene chloride.

Scheme 3

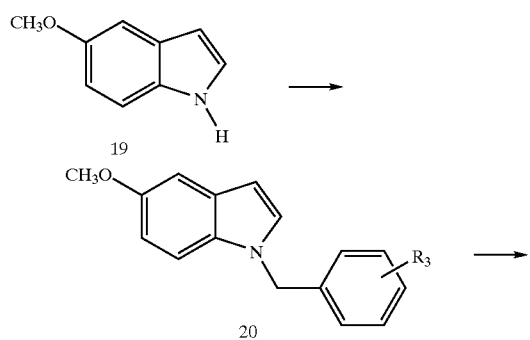

18
-continued

For the glyoxylamides substituted in the 5-position with oxybutanoic acid and in the 2-position with hydrogen, the commerically available indole, 19 was converted thru the series of reactions outlined in Scheme 3 to the glyoxylamide 24 using reaction conditions similar to that described in Scheme 1.

Scheme 4

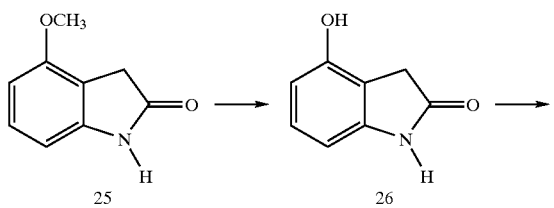

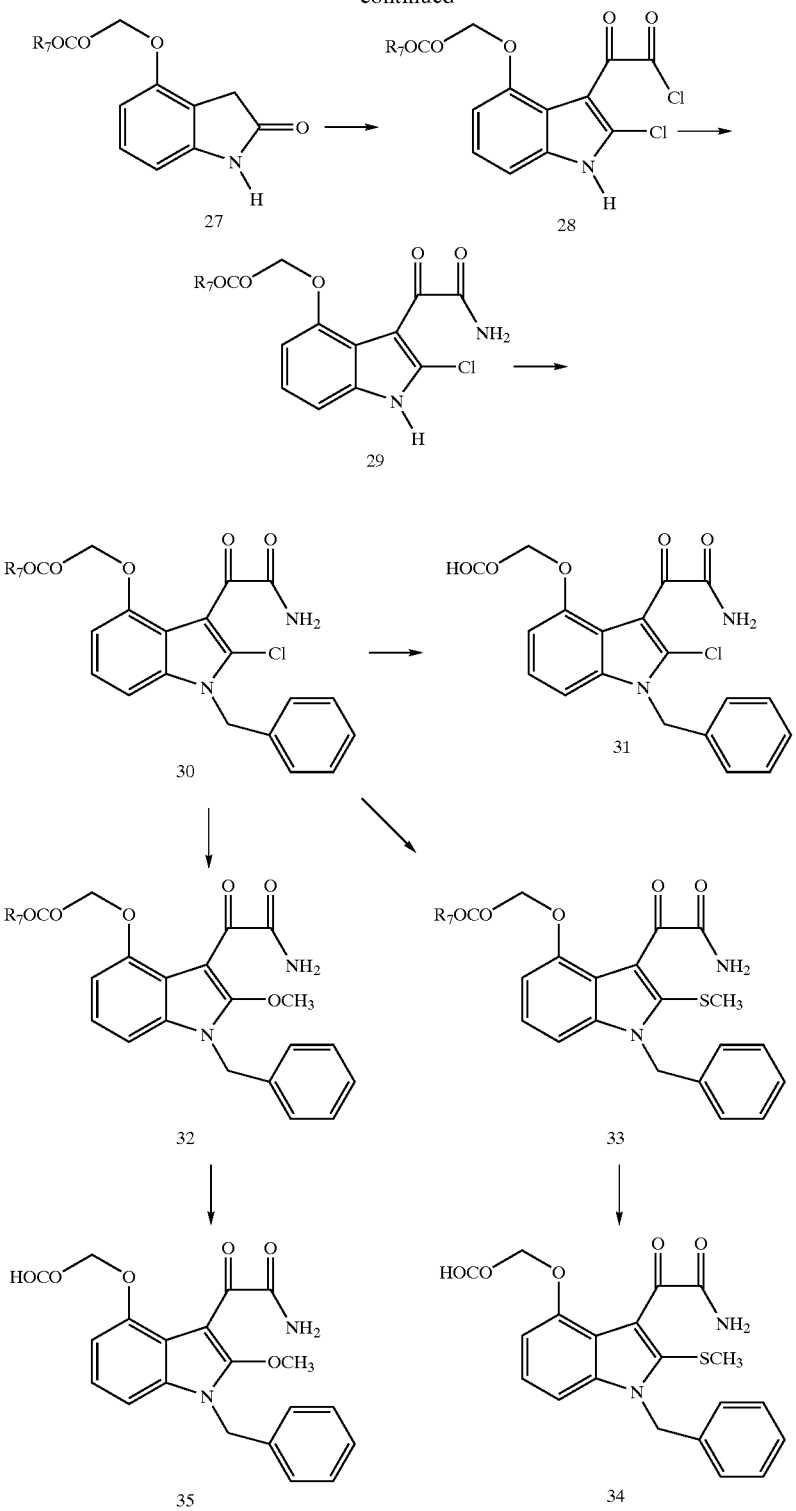

To obtain glyoxylamides substituted in the 4-position with an acid function through an oxygen atom and in the 2-position with chloro, methoxy or methythio, the reactions outlined in Scheme 4 can be used. The 2-oxindole 25 can be converted to the 4-oxyester 27 by methods described in Scheme 1. This intermediate on treatment with oxalyl chloride followed by ammonia gives the glyoxamide 29. Alkylation with benzyl bromide and sodium hydride followed by hydrolysis, would give the 2-chloro acid derivative, 31. Utilizing the intermediate 30, the 2-chloro substituent could be replaced by methymercaptan or methanol to give the 2-methylthio and 2-methoxy derivatives, 34 and 35.

Scheme 5

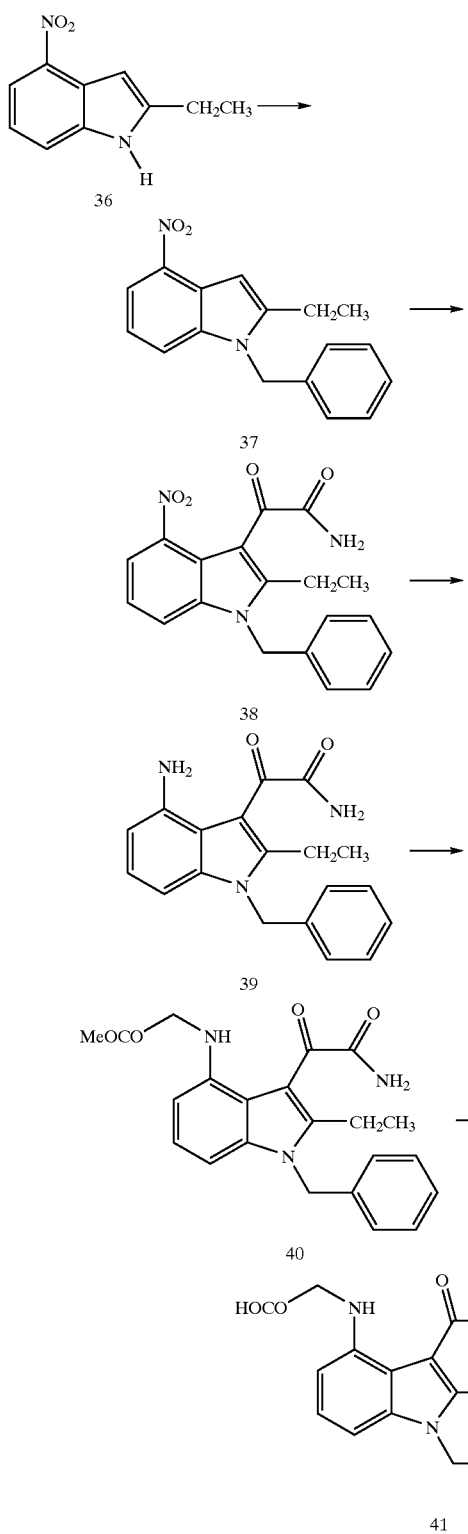

To obtain the glyoxylamides where the carboxyl group in the four position is connected through a nitrogen atom, the reaction sequence in Scheme 5 can be used. The nitro indole (36) (obtained by the procedure outlined in Tetrahedron 46(17) 6085–6112 (1990) by Jan Bergman and Peter Sand, the disclosure of which is incorporated herein by reference) can be alkylated with an arylmethyl bromide using NaH as base to give (37). Treatment of (37) with oxalyl chloride and then ammonia gives the glyoxylamide (38). Reduction of the nitro group of (38) with hydrogen using Pt/BaSO$_4$ as catalyst and subsequent alkylation with a 2-bromoacetate using NaHCO$_3$ as base gives (40). Basic hydrolysis using dilute NaOH gives the product (41).

Scheme 6

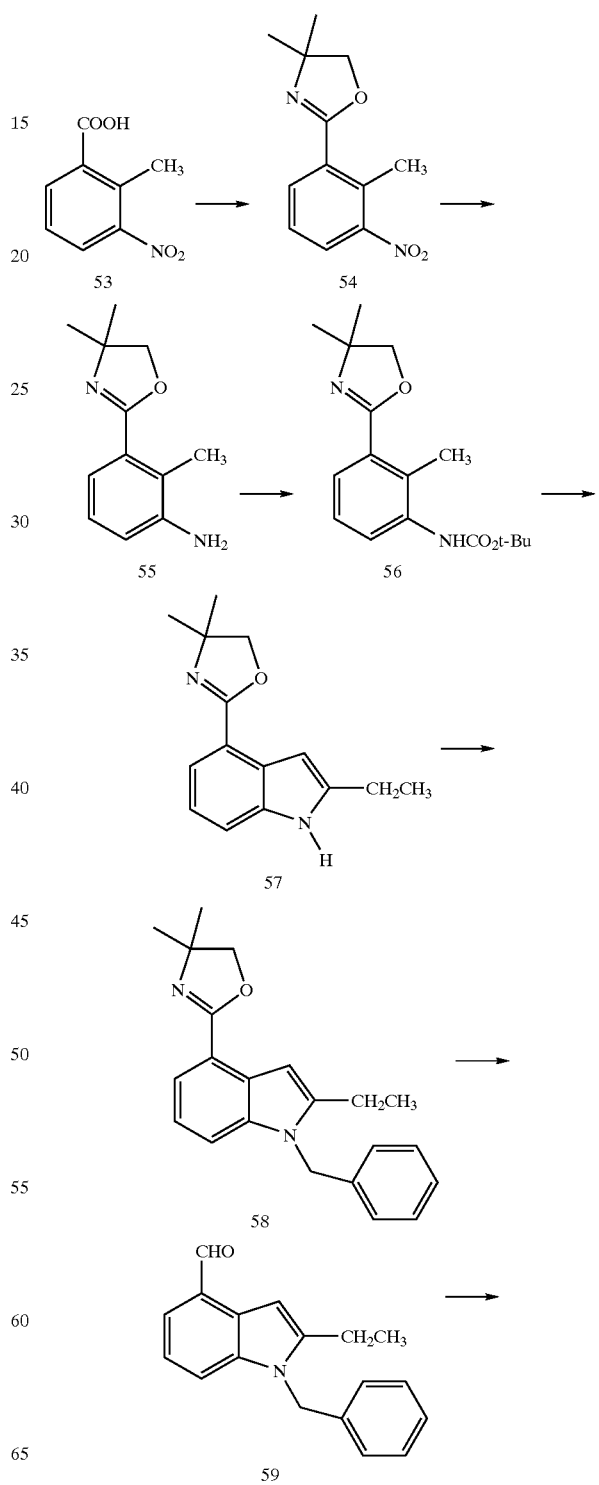

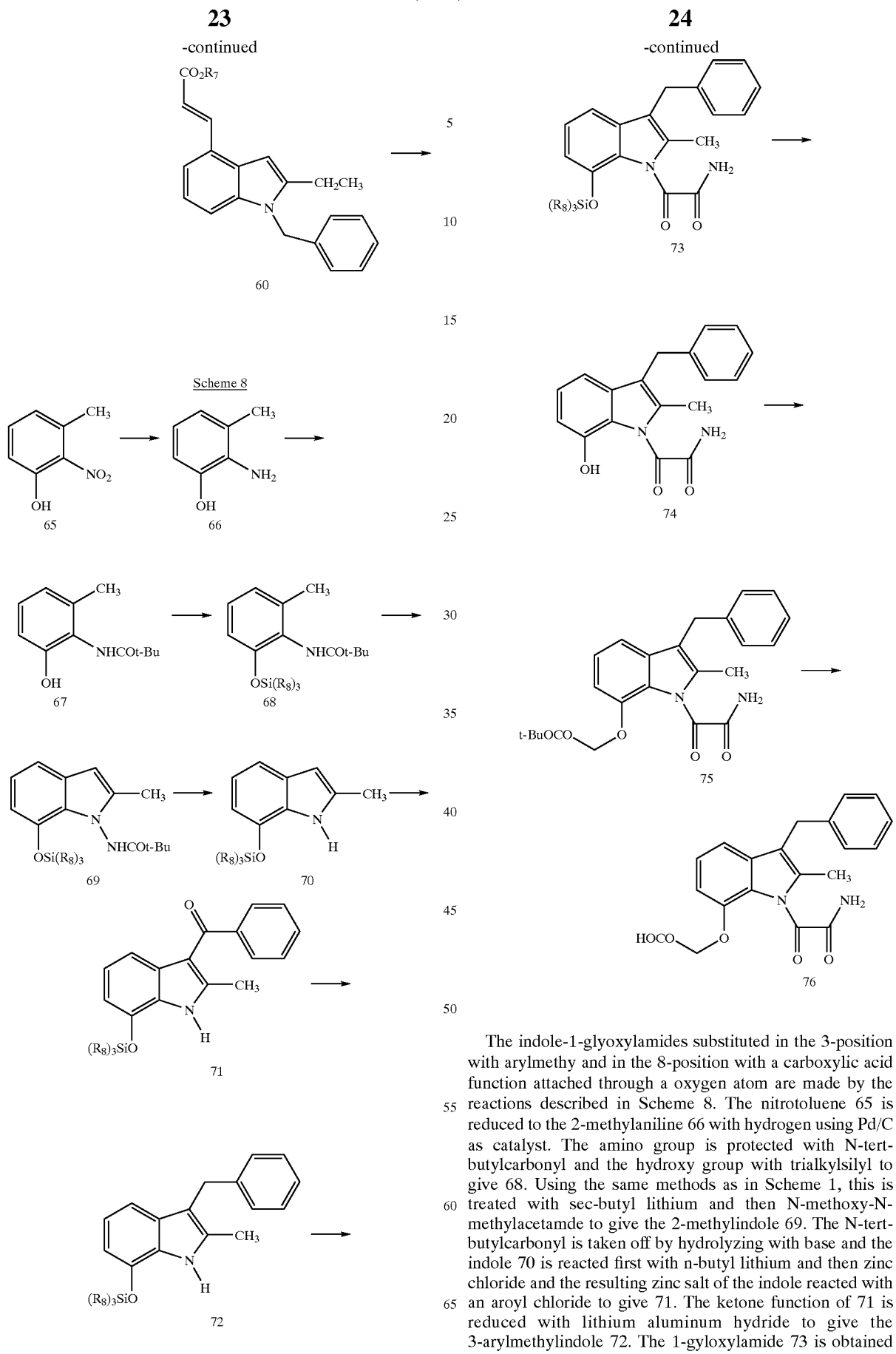

The indole-1-glyoxylamides substituted in the 3-position with arylmethy and in the 8-position with a carboxylic acid function attached through a oxygen atom are made by the reactions described in Scheme 8. The nitrotoluene 65 is reduced to the 2-methylaniline 66 with hydrogen using Pd/C as catalyst. The amino group is protected with N-tert-butylcarbonyl and the hydroxy group with trialkylsilyl to give 68. Using the same methods as in Scheme 1, this is treated with sec-butyl lithium and then N-methoxy-N-methylacetamde to give the 2-methylindole 69. The N-tert-butylcarbonyl is taken off by hydrolyzing with base and the indole 70 is reacted first with n-butyl lithium and then zinc chloride and the resulting zinc salt of the indole reacted with an aroyl chloride to give 71. The ketone function of 71 is reduced with lithium aluminum hydride to give the 3-arylmethylindole 72. The 1-gyloxylamide 73 is obtained by reacting the sodium salt of 72 with oxalyl chloride and then ammonia. Removing the silyl protecting group with tetrabutylammonium fluoride and alkylating the intermediate phenolic compound 74 with sodium hydride and then tert-butyl 2-bromoacetate gives the ester 75. Treatment of this ester with trifluoroacetic acid gives the carboxylic acid derivative 76.

Therapeutic Use of 1H-indole-3-glyoxylamides 1H-indole-3-glyoxylamides described herein are believed to achieve their beneficial therapeutic action principally by direct inhibition of human $sPLA_2$, and not by acting as antagonists for arachidonic acid, nor other active agents below arachidonic acid in the arachidonic acid cascade, such as 5-lipoxygenases, cyclooxygenases, and etc.

The method of the invention for inhibiting $sPLA_2$ mediated release of fatty acids comprises contacting $sPLA_2$ with an therapeutically effective amount of 1H-indole-3-glyoxylamide substituted at the 4 or 5 positions with an acidic derivative, its salt or a prodrug derivative thereof.

A preferred method of the invention comprises contacting $sPLA_2$ with an therapeutically effective amount of 1H-indole-3-glyoxylamide represented by formulae (I) or (II).

A most preferred method of the invention comprises contacting $sPLA_2$ with an therapeutically effective amount of 1H-indole-3-glyoxylamide represented by formulae (I) or (II) where said glyoxylamide is substituted at the 4 position with an acidic group (or salts or prodrug derivatives thereof).

Another aspect of this invention is a method for treating septic shock, adult respiratory distress syndrome, panceatitis, trauma, bronchial asthma, allergic rhinitis, rheumatoid arthritis, and related diseases which comprises administering to a human a therapeutically effective dose of 1H-indole-3-glyoxylamides of the invention or a pharmaceutically acceptable salt or prodrug derivative thereof.

Pharmaceutical Formulations of the Invention

As previously noted the compounds of this invention are useful for inhibiting $sPLA_2$ mediated release of fatty acids such as arachidonic acid. By the term, "inhibiting" is meant the prevention or therapeutically significant reduction in release of $sPLA_2$ initiated fatty acids by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the 1H-indole-3-glyoxylamides of the invention together with a pharmaceutically acceptable carrier or diluent therefor. The present pharmaceutical formulations are prepared by known procedures using well known and readily available ingredients.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act a flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents for example, gelatin or acacia, and lubricating agents such as magnesium stearate, stearic acid, or talc.

In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from about 1 to about 99 weight percent of the active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The active ingredient can be dissolved or suspended in a pharmaceutically acceptable carrier, such as sterile water, sterile organize solvent or a mixture of both. The active ingredient can often be dissolved in a suitable organic solvent, for instance aqueous propylene glycol. Other compositions can be made by dispersing the finely divided active ingredient in aqueous starch or sodium carboxymethyl cellulose solution or in a suitable oil.

The following pharmaceutical formulations 1 thru 8 are illustrative only and are not intended to limit the scope of the invention in any way. "Active ingredient", refers to a compound according to Formula (I) or a pharmaceutically acceptable salt, solvate, or prodrug thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which after mixing, are compressed on a tablet machine to yield tablets each weighing 150 mg.

Formulation 5

Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |

| | |
|---|---|
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active ingredient | 100 mg |
| Isotonic saline | 1,000 ml |

The solution of the above ingredients generally is administered intravenously to a subject at a rate of 1 ml per minute.

All of the products of the Examples described below as well as intermediates used in the following procedures showed satisfactory nmr and ir spectra. They also had the correct mass spectral values.

EXAMPLES

Example 1

Preparation of [[3-(2-Amino-1,2-dioxoethyl)-2-methyl-1-(phenylmethyl)-1H-indol-4-yl]oxy]acetic Acid, a Compound Represented by the Formula

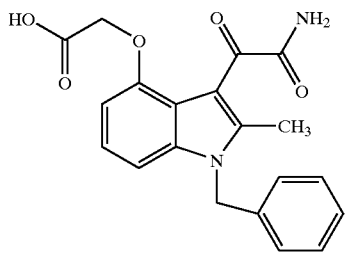

Part A. Preparation of N-tert-butoxycarbonyl-3-methoxy-2-methylaniline

A solution of 44.4 g (344 mmol) of 3-methoxy-2-methylaniline and 75 g (344 mmol) of di-tert-butyl dicarbonate in 400 mL of THF was heated to maintain reflux for 4 hours. After concentrating at reduced pressure, the residue was taken up in ethyl acetate, washed with 1N citric acid, water and dried ($MgSO_4$). After removing the solvent at reduced pressure, the residue was crystallized from hexane to give 64.5 g (84% yield) of N-tert-butoxycarbonyl-3-methoxy-2-methylaniline, mp, 56–57° C.

Analysis for $C_{13}H_{19}NO_3$: Calculated: C, 65.80; H, 8.07; N, 5.90. Found: C, 63.32; H, 7.83; N, 5.56.

Part B. Preparation of 4-Methoxy-2-methyl-1H-indole

A solution of 280 mL (0.36 mol) of 1.3M sec-butyl lithium in cyclohexane was added slowly to N-tert-butoxycarbonyl-3-methoxy-2-methylaniline (43 g, 0.18 mol) in 300 mL of THF keeping the temperature below −40° C. with a dry ice-ethanol bath. The bath was removed and the temperature allowed to rise to −20° C. and then the bath replaced. After the temperature had cooled to −60° C., 18.5 g (0.18 mol) of N-methoxy-N-methylglyoxylamide in an equal volume of THF was added dropwise. The reaction mixture was stirred 1 hour, the cooling bath removed and stirred an additional 1 hour. It was then poured into a mixture of 600 mL of ether and 600 mL of 1N HCl. The organic layer was separated, washed with water, dried over $MgSO_4$, and concentrated at reduced pressure to give 39.5 g of a mixture of 1-[2-(tert-butoxycarbonylamino)-6-methoxyphenyl]-2-propanone and starting anilide. This mixture was dissolved in 100 mL of methylene chloride and 40 mL of trifluoroacetic acid and stirred for a total of 26 hours. The mixture was washed with water, dried ($MgSO_4$) and concentrated at reduced pressure. The residue was chromatographed on silica gel eluting with 20% EtOAc/hexane to give on crystallization from $CH_2Cl_2$/hexane 13.9 g of 4-methoxy-2-methyl-1H-indole, mp, 80–86° C.

Analysis for $C_{10}H_{11}NO$: Calculated: C, 74.51; H, 6.88; N, 8.69. Found: C, 74.41; H, 7.08; N, 8.47.

Part C. Preparation of 4-Methoxy-2-methyl-1-(phenylmethyl)-1H-indole

4-Methoxy 2-methyl-1H-indole (1 g, 6.2 mmol) was added to 248 mg (6.2 mmol)) of 60% sodium hydride/mineral oil (washed with hexane before adding DMF) in 15 mL of DMF and after stirring for 0.5 hour, 0.74 mL (6.2 mmol) of benzyl bromide was added. The mixture was stirred at room temperature for 18 hours, diluted with water and extracted with ethyl acetate. The ethyl acetate solution was washed with brine, dried ($MgSO_4$) and after concentrating at reduced pressure, the residue was chromatographed on silica gel eluting with 20% EtOAc/hexane to give 1.3 g (84% yield) of 4-methoxy-2-methyl-1-(phenylmethyl)-1H-indole, melting at 96–116° C.

Analyses for $C_{17}H_{17}NO$: Calculated: C, 81.24; H, 6.82; N, 5.57. Found: C, 81.33; H, 6.74; N, 5.29.

Part D. Preparation of 4-Hydroxy-2-methyl-1-(phenylmethyl)-1H-indole

A solution of 1.25 g (5 mmol) of 4-methoxy-2-methyl-1-(phenylmethyl)-1H-indole and 20 mL of 1M $BBr_3$/$CH_2Cl_2$ in 50 mL of methylene chloride was stirred at room temperature for 5 hours and concentrated at reduced pressure. The residue was dissolved in ethyl acetate, washed with brine and dried ($MgSO_4$). After concentrating at reduced pressure, the residue was chromatographed on silica gel eluting with 20% EtOAc/hexane to give 577 mg (49% yield) of 4-hydroxy-2-methyl-1-(phenylmethyl)-1H-indole, 125–127° C.

Analyses for $C_{16}H_{15}NO$: Calculated: C, 80.98; H, 6.37; N, 5.90. Found: C, 80.76; H, 6.26; N, 5.80.

Part E. Preparation of [[2-Methyl-1-(phenylmethyl)-1H-indol-4-yl]oxy]acetic Acid Methyl Ester 4-Hydroxy-2-methyl-1-(phenylmethyl)-1H-indole (530 mg, 2.2 mmol) was added to 88 mg (2.2 mmol) of 60% NaH/mineral oil in 20 mL of DMF and the mixture stirred for 0.67 hours. Then, 0.21 mL (2.2 mmol) of methyl bromoacetate was added and stirring maintained for 17 hours. The mixture was diluted with water and extracted with ethyl acetate. The ethyl acetate solution was washed with brine, dried (MgSO$_4$), and concentrated at reduced pressure. The residue was chromatographed on silica gel eluting with 20% EtOAc/hexane to give 597 mg (88% yield) of [[2-methyl-1-(phenylmethyl)-1H-indol-4-yl]oxy]acetic acid methyl ester, 140–143° C.

Analyses for C$_{29}$H$_{19}$NO$_3$: Calculated: C, 73.77; H, 6.19; N, 4.53. Found: C, 74.01; H, 6.23; N, 4.32.

Part F. Preparation of [[3-(2-Amino-1,2-dioxoethyl)-2-methyl-1-(phenylmethyl)-1H-indol-4-yl]oxy]acetic Acid Methyl Ester Oxalyl chloride (0.16 mL, 1.9 mmol) was added to 582 mg (1.9 mmol) of [[2-methyl-1-(phenylmethyl)-1H-indol-4-yl]oxy]acetic acid methyl ester in 10 mL of methylene chloride and the mixture stirred for 1.5 hours. The mixture was concentrated at reduced pressure and residue taken up in 10 mL of methylene chloride. Anhydrous ammonia was bubbled in for 0.25 hours, the mixture stirred for 1.5 hours and evaporated at reduced pressure. The residue was stirred with 20 mL of ethyl acetate and the mixture filtered. The filtrate was concentrated to give 672 mg of a mixture of [[3-(2-amino-1,2-dioxoethyl)-2-methyl-1-(phenylmethyl)-1H-indol-4-yl]oxy]acetic acid, methyl ester and ammonium chloride, mp 202–215° C.

Part G. Preparation of [[3-(2-Amino-1,2-dioxoethyl)-2-methyl-1-(phenylmethyl)-1H-indol-4-yl]oxy]acetic Acid A mixture of 660 mg (1.7 mmol) of [[3-(2-amino-1,2-dioxoethyl)-2-methyl-1-(phenylmethyl)-1H-indol-4-yl]oxy]acetic acid methyl ester and 10 mL of 1N NaOH in 30 mL of methanol was heated to maintain reflux for 1 hour, cooled to room temperature and stirred for 0.5 hour. The mixture was concentrated at reduced pressure and the residue taken up in EtOAc/water. The aqueous layer was separated, made acidic to pH 2–3 with 1N HCl and extracted with EtOAc. On concentrating the EtOAc solution, 431 mg (69% yield) of [[3-(2-amino-1,2-dioxoethyl)-2-methyl-1-(phenylmethyl)-1H-indol-4-yl]oxy]acetic acid crystallized, melting at 218–220° C.

Analyses for C$_{20}$H$_{18}$N$_2$O$_5$: Calculated: C, 65.57; H, 4.95; N, 7.65. Found: C, 63.31; H, 4.79; N, 6.91.

Example 2

Preparation of dl-2-[[3-(2-Amino-1,2-dioxoethyl)-2-methyl-1-(phenylmethyl)-1H-indol-4-yl]oxy]propanoic Acid, a Compound Represented by the Formula

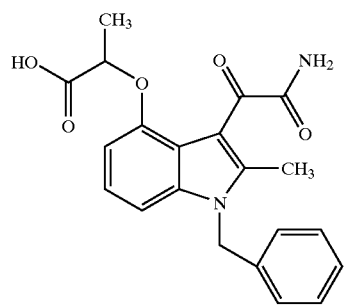

Part A. Preparation of dl-2-[[2-Methyl-1-(phenylmethyl)-1H-indol-4-yl]oxy]propanoic Acid Methyl Ester 4-Hydroxy-2-methyl-1-(phenylmethyl)-1H-indole (483 mg, 2.0 mmol) was reacted with 82 mg (2.0 mmol) of 60% NaH/mineral oil in 20 mL of DMF and then with 0.22 mL (2.0 mmol) of dl-methyl 2-bromopropionate as described in Example 1, Part E to give after chromatography on silica gel eluting with 20% EtOAc/hexane 480 mg (74% yield) of dl-2-[[2-methyl-1-(phenylmethyl)-1H-indol-4-yl]oxy] propanoic acid methyl ester.

Part B. Preparation of dl-2-[[3-(2-Amino-1,2-dioxoethyl)-2-methyl-1-(phenylmethyl)-1H-indol-4-yl]oxy]propanoic Acid, Methyl Ester Oxalyl chloride (0.16 mL, 1.9 mmol) was reacted with 480 mg (1.5 mmol) of dl-2-[[2-methyl-1-(phenylmethyl)-1H-indol-4-yl]oxy]propanoic acid methyl ester and then reacted with anhydrous ammonia as in Example 1, Part F and the reaction product was dissolved in EtOAc, washed with water, dried (MgSO$_4$) and concentrated. The residue was chromatographed on silica gel (elated with EtOAc) to give 531 mg (90% yield) of dl-2-[[3-(2-amino-1,2-dioxoethyl)-2-methyl-1-(phenylmethyl)-1H-indol-4-yl]oxy] propanoic acid, methyl ester, melting at approximately 175° C.

Analyses for C$_{22}$H$_{22}$N$_2$O$_5$: Calculated: C, 66.99; H, 5.62; N, 7.10. Found: C, 67.28; H, 5.59; N, 7.03.

Part C. Preparation of dl-2-[[3-(2-Amino-1,2-dioxoethyl)-2-methyl-1-(phenylmethyl)-1H-indol-4-yl]oxy]propanoic Acid A mixture of 521 mg (1.3 mmol) of dl-2-[[3-(2-amino-1,2-dioxoethyl)-2-methyl-1-(phenylmethyl)-1H-indol-4-yl]oxy]propanoic acid methyl ester and 10 mL of 1N NaOH in 30 mL of methanol was heated to maintain reflux for 0.17 hours, cooled to room temperature and stirred for 0.5 hour. The mixture was concentrated at reduced pressure and the residue taken up in EtOAc/water. The aqueous layer was separated, made acidic to pH 2–3 with 1N HCl and extracted with EtOAc. The EtOAc solution was concentrated at reduced pressure and the residue stirred with a EtOAc-ether mixture. The insoluble material was filtered to give 246 mg (50% yield) of dl-2-[[3-(2-amino-1,2-dioxoethyl)-2-methyl-1-(phenylmethyl)-1H-indol-4-yl]oxy]propanoic acid, mp, 201–204° C.

Analyses for C$_{21}$H$_{20}$N$_2$O$_5$:

Calculated: C, 66.31; H, 5.30; N, 7.36.

Found: C, 65.63; H, 5.61; N, 7.03.

Example 3

Preparation of [[3-(2-Amino-1,2-dioxoethyl)-1-([1,1'-biphenyl]-2-ylmethyl)-2-methyl-1H-indol-4-yl]oxy]acetic Acid, a Compound Represented by the Formula

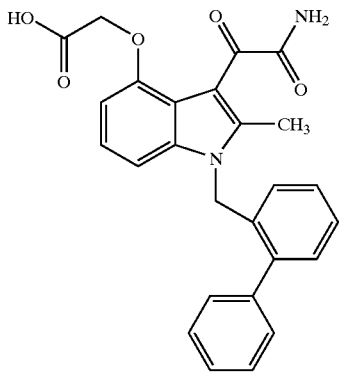

Part A. Preparation of 1-([1,1'-Biphenyl]-2-ylmethyl)-4-methoxy-2-methyl-1H-indole Using the procedure described in Example 1, Part C, 1 g (6.2 mmol) of 4-methoxy-2-methyl-1H-indole was reacted with 248 mg (6.2 mmol) of 60% NaH/mineral oil and then 1.1 mL (6.2 mmol) of 2-(bromomethyl)biphenyl to give after chromatography on silica (eluting with 17% EtOAc/hexane) 1.63 g (80% yield) of 1-([1,1'-biphenyl]-2-ylmethyl)-4-methoxy-2-methyl-1H-indole as an oil.

Analyses for $C_{23}H_{21}NO$:
Calculated: C, 84.37; H, 6.46; N, 4.28.
Found: C, 84.11; H, 5.66; N, 3.83.

Part B. Preparation of 1-([1,1'-Biphenyl]-2-ylmethyl)-4-hydroxy-2-methyl-1H-indole By the method used in Example 1, Part D, 1.6 g (4.9 mmol) of 1-([1,1'-biphenyl]-2-ylmethyl)-4-methoxy-2-methyl-1H-indole was O-demethylated by treating it with 20 mL of 1M $BBr_3/CH_2Cl_2$. The crude product was chromatographed on silica gel and eluted with 20% EtOAc/hexane to give 841 mg (55% yield) of 1-([1,1'-biphenyl]-2-ylmethyl)-4-hydroxy-2-methyl-1H-indole Analyses for $C_{22}H_{19}NO$:
Calculated: C, 84.32; H, 6.11; N, 4.47.
Found: C, 84.59; H, 6.33; N, 4.75.

Part C. Preparation of [[1-([1,1'-Biphenyl]-2-ylmethyl)-2-methyl-1H-indol-4-yl]oxy]acetic Acid Methyl Ester 1-([1,1'-Biphenyl]-2-ylmethyl)-4-hydroxy-2-methyl-1H-indole (767 mg, 2.45 mmol) was alkylated by treating with 0.23 mL (2.45 mmol) of methyl bromoacetate and 98 mg (2.45 mmol) of 60% NaH/mineral oil in DMF as described in Example 1, Part E. The product was purified by chromatography over silica gel eluting with 20% EtOAc/hexane, to give 730 mg (77% yield) of [[1-([1,1'-biphenyl]-2-ylmethyl)-2-methyl-1H-indol-4-yl]oxy]acetic acid methyl ester, 99–101° C.

Analyses for $C_{25}H_{23}NO_3$:
Calculated: C, 77.90; H, 6.01; N, 3.63.
Found: C, 78.11; H, 6.17; N, 3.74.

Part D. Preparation of [[3-(2-Amino-1,2-dioxoethyl)-1-([1,1'-biphenyl]-2-ylmethyl)-2-methyl-1H-indol-4-yl]oxy]acetic Acid Methyl Ester Using the procedure in Example 1, Part F, 715 mg (1.9 mmol) of [[1-(1,1'-biphenyl]-2-ylmethyl)-2-methyl-1H-indol-4-yl]oxy]acetic acid methyl ester was reacted first with 0.16 mL (1.9 mmol) of oxalyl chloride and then excess ammonia to give a white solid. This was stirred with ethyl acetate and the insoluble material separated and dried to give 660 mg of a mixture of [[3-(2-amino-1,2-dioxoethyl)-1-([1,1'-biphenyl]-2-ylmethyl)-2-methyl-1H-indol-4-yl]oxy] acetic acid methyl ester and ammonium chloride. This mixture melted at 144–148° C.

Part E. Preparation of [[3-(2-Amino-1,2-dioxoethyl)-1-([1,1'-biphenyl]-2-ylmethyl)-2-methyl-1H-indol-4-yl]oxy]acetic Acid A mixture of 648 mg (1.4 mmol) of [[3-(2-amino-1,2-dioxoethyl)-1-([1,1'-biphenyl]-2-ylmethyl)-2-methyl-1H-indol-4-yl]oxy]aceti(c acid methyl ester in 10 mL of 1N NaOH and 20 mL of MeOH was heated to maintain reflux for 1 hour, cooled to room temperature and stirred 0.5 hour. The mixture was concentrated, the residue stirred with a mixture of EtOAc/water and the solid material that did not dissolve was filtered and dried to give 227 mg (35% yield) of [[3-(2-amino-1,2-dioxoethyl)-1-([1,1'-biphenyl]-2-ylmethyl)-2-methyl-1H-indol-4-yl]oxy]acetic acid, sodium salt, mp, >265° C.

Analyses for $C_{26}H_{21}N_2O_5Na$:
Calculated: C, 67.24; H, 4.56; N, 6.03.
Found: C, 69.38; H, 4.88; N, 5.42.

Part F.

The aqueous layer was separated from the filtrate from above and made acidic to pH 2–3 with 1N HCl. The precipitate was extracted with EtOAc and upon concentrating the EtOAc, 128 mg (20% yield) of [[3-(2-amino-1,2-dioxoethyl)-1-([1,1'-biphenyl]-2-ylmethyl)-2-methyl-1H-indol-4-yl]oxy]acetic acid precipitated, mp, 228–231° C.

Analyses for $C_{26}H_{22}N_2O_5$:
Calculated: C, 70.58; H, 5.01; N, 6.33.
Found: C, 73.12; H, 5.37; N, 5.81.

Example 4

Preparation of [[3-(2-Amino-1,2-dioxoethyl)-1-([1,1'-biphenyl]-3-ylmethyl)-2-methyl-1H-indol-4-yl]oxy]acetic Acid, a Compound Represented by the Formula

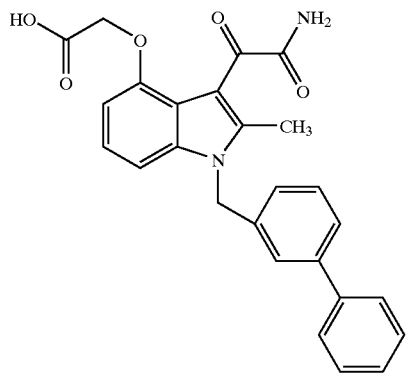

Part A. Preparation of 1-([1,1'-Biphenyl]-3-ylmethyl)-4-methoxy-2-methyl-1H-indole Using the method in Example 1, Part C, 805 mg (5 mmol) of 4-methoxy-2-methyl-1H-indole was reacted with 200 mg (5 mmol) of 60% NaH/mineral and then 1.0 g(5 mmol) of 3-(chloromethyl)biphenyl in DMF to give after chromatography on silica gel (eluted with 20% EtOAc/hexane) 1.25 g (76% yield) of 1-([1,1'-biphenyl]-3-ylmethyl)-4-methoxy-2-methyl-1H-indole, mp, 127–131° C.

Analyses for $C_{23}H_{21}NO$:
Calculated: C, 84.37; H, 6.46; N, 4.27.
Found: C, 83.30; H, 6.55; N, 4.07.

Part B. Preparation of 1-([1,1'-Biphenyl]-3-ylmethyl)-4-hydroxy-2-methyl-1H-indole By the method used in Example 1, Part D, 1.25 g (3.8 mmol) of 1-([1,1'-biphenyl]-3-ylmethyl)-4-methoxy-2-methyl-1H-indole was O-demethylated by treating it with 15.2 mL of 1M $BBr_3/CH_2Cl_2$ to give 1.03 g (87% yield) of crude 1-([1,1'-biphenyl]-3-ylmethyl)-4-hydroxy-2-methyl-1H-indole.

Part C. Preparation of [[1-([1,1'-Biphenyl]-3-ylmethyl)-2-methyl-1H-indol-4-yl]oxy]acetic Acid Methyl Ester 1-([1,1'-Biphenyl]-3-ylmethyl)-4-hydroxy-2-methyl-1H-indole (1.03 g, 3.3 mmol) was alkylated by treating with 0.31 mL (3.3 mmol) of methyl bromoacetate and 132 mg (3.3 mmol) of 60% NaH/mineral oil in DMF as described in Example 1, Part E. The product was purified by chromatography over silica gel eluting with 20% EtOAc/hexane, to give 1.0 g (79% yield) of [[1-([1,1'-biphenyl]-3-ylmethyl)-2-methyl-1H-indol-4-yl]oxy]acetic acid methyl ester, 99–102° C.

Analyses for $C_{25}H_{23}NO_3$:
Calculated: C, 77.90; H, 6.01; N, 3.63.
Found: C, 77.61; H, 6.09; N, 3.62.

Part D. Preparation of [[3-(2-Amino-1,2-dioxoethyl)-1-([1,1'-biphenyl]-3-ylmethyl)-2-methyl-1H-indol-4-yl]oxy]acetic Acid Methyl Ester Oxalyl chloride (0.23 mL, 2.6 mmol) was added to 1.0 g (2.6 mmol) of [[1-([1,1'-biphenyl]-3-ylmethyl)-2-methyl-1H-indol-4-yl]oxy]acetic acid methyl ester in 15 mL of methylene chloride and the mixture stirred for 1.3 hours. The mixture was concentrated at reduced pressure, the residue redissolved in 15 mL of methylene chloride and ammonia gas bubbled in for 0.25 hours, stirred for 0.25 hours and concentrated. The residue was stirred with EtOAc/water and the undissolved material filtered to give 300 mg of [[3-(2-amino-1,2-dioxoethyl)-1-([1,1 '-biphenyl]-3-ylmethyl)-2-methyl-1H-indol-4-yl]oxy]acetic acid methyl ester. The EtOAc layer from the filtrate was separated, washed with brine, dried(MgSO$_4$) and concentrated. The residue was chromatographed on silica gel eluting with EtOAc to give an additional 671 mg of [[3-(2-amino-1,2-dioxoethyl)-1-([1,1'-biphenyl]-3-ylmethyl)-2-methyl-1H-indol-4-yl]oxy]acetic acid methyl ester, mp, 175–179° C. The total combined yield of product was 82%.

Analyses for $C_{27}H_{24}N_2O_5$:
Calculated: C, 71.04; H, 5.30; N, 6.14.
Found: C, 71.30; H, 5.41; N, 6.35.

Part E. Preparation of [[3-(2-Amino-1,2-dioxoethyl)-1-([1,1'-biphenyl]-3-ylmethyl)-2-methyl-1H-indol-4-yl]oxy]acetic Acid Using the procedure described in Example 2, Part E, 956 mg (2.1 mmol) of ([[3-(2-amino-1,2-dioxoethyl)-1-([1,1'-biphenyl]-3-ylmethyl)-2-methyl-1H-indol-4-yl]oxy]acetic acid methyl ester was hydrolyzed in 10 mL of 1N NaOH and 20 mL of MeOH to give 403 mg (415% yield) of [[3-(2-amino-1,2-dioxoethyl)-1-([1,1'-biphenyl]-3-ylmethyl)-2-methyl-1H-indol-4-yl]oxy]acetic acid, sodium silt, mp, >265° C.

Analyses for $C_{26}H_{21}N_2O_5Na$:
Calculated: C, 67.24; H, 4.56; N, 6.03.
Found: C, 67.20; H, 4.58; N, 6.03.

There was also obtained 346 mg (37% yield) of [[3-(2-amino-1,2-dioxoethyl)-1-([1,1'-biphenyl]-3-ylmethyl)-2-methyl-1H-indol-4-yl]oxy]acetic acid, mp, 236–238° C.

Analyses for $C_{26}H_{22}N_2O_5$:
Calculated: C, 70.58; H, 5.01; N, 6.33.
Found: C, 70.58; H, 5.25; N, 6.11.

Example 5

Preparation of [[3-(2-Amino-1,2-dioxoethyl)-1-([1,1'-biphenyl]-4-ylmethyl)-2-methyl-1H-indol-4-yl]oxy]acetic Acid, a Compound Represented by the Formula

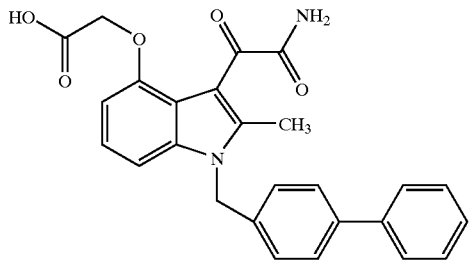

Part A. Preparation of 1-([1,1'-Biphenyl]-4-ylmethyl)-4-methoxy-2-methyl-1H-indole Using the method in Example 1, Part C, 805 mg (5 mmol) of 4-methoxy-2-methyl-1H-indole was reacted with 200 mg (5 mmol) of 60% NaH/mineral oil and then 1.0 g (5 mmol) of 4-(chloromethyl)phenyl in DMF to give after chromatography on silica gel (eluted with 20% EtOAc/hexane) 1.3 g (80% yield) of 1-([1,1'-biphenyl]-4-ylmethyl)-4-methoxy-2-methyl-1H-indole, mp, 118–123° C.

Analyses for $C_{23}H_{21}NO$:
Calculated: C, 84.37; H, 6.46; N, 4.27.
Found: C, 84.66; H, 6.62; N, 4.00.

Part B. Preparation of 1-([1,1'-Biphenyl]-4-ylmethyl)-4-hydroxy-2-methyl-1H-1H-indole By the method used in Example 1, Part D, 1.3 g (4.0 mmol) of 1-([1,1'-biphenyl]-4-ylmethyl)-4-methoxy-2-methyl-1H-indole was O-demethylated by treating it with 16 mL of 1M $BBr_3/CH_2Cl_2$ to give 970 mg (77% yield) of crude 1-([1,1'-biphenyl]-4-ylmethyl)-4-hydroxy-2-methyl-1H-indole.

Part C. [[1-([1,1'-Biphenyl]-4-ylmethyl)-2-methyl-1H-indol-4-yl]oxy]acetic Acid Methyl Ester Using the procedure described in Example 1, Part E, 1-([1,1-biphenyl]-3-ylmethyl)-4-hydroxy-2-methyl-1H-indole (970 mg, 3.1 mmol) was treated with 124 mg (3.1 mmol) of 60% NaH/mineral oil and then 0.29 mL (3.1 mmol) of methyl bromoacetate. The product was purified by chromatography over silica gel eluting with 20% EtOAc/hexane, to give 747 mg (63% yield) of [[1-([1,1'-biphenyl]-4-ylmethyl)-2-methyl-1H-indol-4-yl]oxy]acetic acid methyl ester, 164–167° C.

Analyses for $C_{25}H_{23}NO_3$:

Calculated: C, 77.90; H, 6.01; N, 3.63.

Found: C, 78.83; H, 6.10; N, 3.56.

Part D. Preparation of [[3-(2-Amino-1,2-dioxoethyl)-1-([1,1'-biphenyl]-4-ylmethyl)-2-methyl-1H-indol-4-yl]oxy]acetic Acid Methyl Ester Oxalyl chloride (0.17 mL, 1.9 mmol) was added to 747 mg (2.6 mmol) of [[1-([1,1'-biphenyl]-4-ylmethyl)-2-methyl-1H-indol-4-yl]oxy]acetic acid methyl ester in 15 mL of methylene chloride and the mixture stirred for 1.3 hours. The mixture was concentrated at reduced pressure, the residue redissolved in 15 mL of methylene chloride and ammonia gas bubbled in for 0.25 hours, stirred for 0.25 hours and concentrated. The residue was stirred with EtOAc/water and the undissolved material filtered to give 818 mg (94% yield) of [[3-(2-amino-1,2-dioxoethyl)-1-([1,1'-biphenyl]-4-ylmethyl)-2-methyl-1H-indol-4-yl]oxy]acetic acid methyl ester, 215–217° C.

Analyses for $C_{27}H_{24}N_2O_5$:

Calculated: C, 71.04; H, 5.30; N, 6.14.

Found: C, 71.32; H, 5.43; N, 6.33.

Part E. Preparation of [[3-(2-Amino-1,2-dioxoethyl)-1-([1,1'-biphenyl]-4-ylmethyl)-2-methyl-1H-indol-4-yl]oxy]acetic Acid Using the procedure described in Example 2, Part E, 803 mg (1.8 mmol) of [[3-(2-amino-1,2-dioxoethyl)-1-([1,1'-biphenyl]-4-ylmethyl)-2-methyl-1H-indol-4-yl]oxy]acetic acid methyl ester was hydrolyzed in 10 mL of 1N NaOH and 20 mL of MeOH to give 614 mg (741% yield) of [[3-(2-amino-1,2-dioxoethyl)-1-([1,1'-biphenyl]-4-ylmethyl)-2-methyl-1H-indol-4-yl]oxy]acetic acid, sodium salt, mp, >265° C.

Analyses for $C_{26}H_{21}N_2O_5Na$:

Calculated: C, 67.24; H, 4.56; N, 6.03.

Found: C, 67.48; H, 4.62; N, 6.14.

There was also obtained 35 mg (4% yield) of [[3-(2-amino-1,2-dioxoethyl)-1-([1,1'-biphenyl]-4-ylmethyl)-2-methyl-1H-indol-4-yl]oxy]acetic acid, mp, 228–232° C.

Analyses for $C_{26}H_{22}N_2O_5$:

Calculated: C, 70.58; H, 5.01; N, 6.33.

Found: C, 70.54; H, 5.08; N, 6.14.

Example 6

Preparation of [[3-(2-Amino-1,2-dioxoethyl)-1-[(2,6-dichlorophenyl)methyl]-2-methyl-1H-indol-4-yl]oxy]acetic Acid, a Compound Represented by the Formula

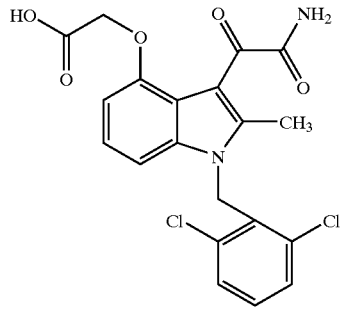

Part A. Preparation of 1-[(2,6-Dichlorophenyl)methyl]-4-methoxy-2-methyl-1H-indole 4-Methoxy-2-methyl-1H-indole (805 mg, 5 mmol) was added to a mixture of 160 mg (4 mmol) of 60% sodium hydride/mineral oil (washed with hexane before adding DMF) in 10 mL of DMF and after stirring for 0.67 hours, 782 mg (4 mmol) of α,2,6-trichlorotoluene was added. The mixture was stirred at room temperature for 5 hours, diluted with water and extracted with ethyl acetate. The ethyl acetate solution was washed with brine, dried ($MgSO_4$) and after concentrating at reduced pressure, the residue was chromatographed on silica gel eluting with 20% EtOAc/hexane to give 1.08 g (84% yield) of 1-[(2,6-dichlorophenyl)methyl]-4-methoxy-2-methyl-1H-indole, melting at 154–57° C.

Analyses for $C_{17}H_{15}Cl_2NO$:
Calculated: C, 63.77; H, 4.72; N, 4.37.
Found: C, 67.16; H, 5.14; N, 4.19.

Part B. Preparation of 1-[(2,6-Dichlorophenyl)methyl]-4-hydroxy-2-methyl-1H-indole By the method used in Example 1, Part D, 1.08 g (3.38 mmol) of 1-[(2,6 dichlorophenyl)methyl]-4-methoxy-2-methyl-1H-indole was O-demethylated by treating it with 13.5 mL of 1M $BBr_3/CH_2Cl_2$ to give 862 mg (83% yield) of 1-[(2,6-dichlorophenyl)methyl]-4-hydroxy-2-methyl-1H-indole, after chromatography on silica gel (eluted with 20% EtOAc/hexane).

Analyses for $C_{16}H_{13}Cl_2NO$:
Calculated: C, 62.76; H, 4.28; N, 4.57.
Found: C, 63.03; H, 4.45; N, 4.56.

Part C. Preparation of [[1-[(2,6-Dichlorophenyl)methyl]-2-methyl-1H-indol-4-yl]oxy]acetic Acid Methyl Ester Using the procedure described in Example 1, Part E, 1-[(2,6-dichlorophenyl)methyl]-4-hydroxy-2-methyl-1H-indole (862 mg, 2.8 mmol) was treated with 112 mg (2.8 mmol) of 60% NaH/mineral oil and then 0.27 mL (2.8 mmol) of methyl bromoacetate. The product was purified by chromatography over silica gel eluting with 20% EtOAc/hexane, to give 411 mg (39% yield) of [[1-[(2,6-dichlorophenyl)methyl]-2-methyl-1H-indol-4-yl]oxy]acetic acid methyl ester, mp, 168–169° C.

Analyses for $C_{19}H_{17}Cl_2NO_3$:

Calculated: C, 60.33; H, 4.53; N, 3.70.

Found: C, 60.55; H, 4.70; N, 3.75.

Part D. Preparation of [[3-(2-Amino-1,2-dioxoethyl)-1-[(2,6-dichlorophenyl)methyl]-2-methyl-1H-indol-4-yl]oxy]acetic Acid Methyl Ester Oxalyl chloride (0.09 mL, 1.07 mmol) was added to 405 mg (1.07 mmol) of [[1-[(2,6-dichlorophenyl)methyl]-2-methyl-1H-indol-4-yl]oxy]acetic acid methyl ester in 10 mL of methylene chloride and the mixture stirred for 3.0 hours. The mixture was concentrated at reduced pressure, the residue redissolved in 15 mL of methylene chloride and ammonia gas bubbled in for 0.25 hours, stirred for 0.25 hours and concentrated. The residue was stirred with EtOAc/water. The EtOAc layer was separated, washed with brine, dried ($MgSO_4$) and concentrated. The residue was chromatographed on silica gel eluting with EtOAc to give 426 mg (88% yield) of [[3-(2-amino-1,2-dioxoethyl)-1-[(2,6-dichlorophenyl)methyl]-2-methyl-1H-indol-4-yl]oxy]acetic acid methyl ester, mp, 200–202° C.

Analyses for $C_{21}H_{18}Cl_2N_2O_5$:

Calculated: C, 56.14; H, 4.04; N, 6.24.

Found: C, 56.39; H, 4.15; N, 6.45.

Part E. Preparation of [[3-(2-Amino-1,2-dioxoethyl)-1-[(2,6-dichlorophenyl)methyl]-2-methyl-1H-indol-4-yl]oxy]acetic Acid A mixture of 420 mg (0.94 mmol) of [[3-(2-amino-1,2-dioxoethyl)-1-[(2,6-dichlorophenyl)methyl]-2-methyl-1H-indol-4-yl]oxy]acetic acid methyl ester, 5 mL of 1N NaOH and 15 mL of MeOH was heated to maintain reflux for 0.17 hours, cooled to room temperature and stirred 0.5 hours. Ethyl acetate and water was added, the aqueous layer separated, made acidic to pH 2–3 with 1N HCl, and the mixture extracted with ethyl acetate two times. The part that was not soluble was filtered. The filtrate was dried ($MgSO_4$) and concentrated. The remaining solid was washed with a small volume of ether/methylene chloride and the insoluble material filtered and combined with the filtered material above to give 351 mg (86% yield) of [[3-(2-amino-1,2-dioxoethyl)-1-[(2,6-dichlorophenyl)methyl]-2-methyl-1H-indol-4-yl]oxy]acetic acid, mp, 236–239° C.

Analyses for $C_{20}H_{16}Cl_2N_2O_5$:

Calculated: C, 55.19; H, 3.70; N, 6.44.

Found: C, 55.34; H, 3.72; N, 6.35.

Example 7

Preparation of [[3-(2-Amino-1,2-dioxoethyl)-1-[4(-fluorophenyl)methyl]-2-methyl-1H-indol-4-yl]oxy] acetic Acid, a Compound Represented by the Formula

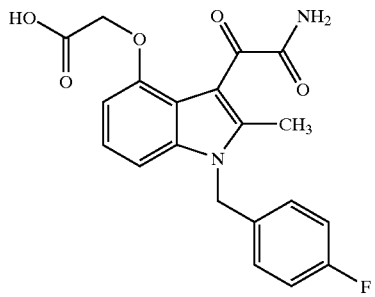

Part A. Preparation of 1-[(4-Fluorophenyl)methyl]-4-methoxy-2-methyl-1H-indole 4-Methoxy-2-methyl-1H-indole (805 mg, 5 mmol) was added to a mixture of 200 mg (5 mmol) of 60% sodium hydride/mineral oil (washed with hexane before adding DMF) in 10 mL of DMF and after stirring for 0.5 hours, 0.6 mL (5 mmol) of 4-fluorobenzyl chloride was added. The mixture was stirred at room temperature for 18 hours, diluted with water and extracted with ethyl acetate. The ethyl acetate solution was washed with brine, dried ($MgSO_4$) and after concentrating at reduced pressure, the residue was chromatographed on silica gel eluting with 20% EtOAc/hexane to give 1.1 g (84% yield) of 1-[(4-fluorophenyl)methyl]-4-methoxy-2-methyl-1H-indole, melting at 104–108° C.

Analyses for $C_{17}H_{16}FNO$:
Calculated: C, 75.82; H, 5.99; N, 5.20.
Found: C, 73.82; H, 5.95; N, 5.01.

Part B. Preparation of 1-[(4-Fluorophenyl)methyl]-4-hydroxy-2-methyl-1H-indole By the method used in Example 1, Part D, 1.1 g (4.1 mmol) of 1-[(4-fluorophenyl)methyl]-4-methoxy-2-methyl-1H-indole was O-demethylated by treating it with 16.4 mL of 1M $BBr_3/CH_2Cl_2$ to give 881 mg (84% yield) of crude 1-[(4-fluorophenyl)methyl]-4-hydroxy-2-methyl-1H-indole.

Part C. Preparation of [[1-[(4-Fluorophenyl)methyl]-2-methyl-1H-indol-4-yl]oxy]acetic Acid Methyl Ester Using the procedure described in Example 1, Part E, 1-[(4-fluorophenyl)methyl]-4-hydroxy-2-methyl-1H-indole (881 mg, 3.45 mmol) was treated with 138 mg (3.45 mmol) of 60% NaH/mineral oil and then 0.33 mL (3.45 mmol) of methyl bromoacetate. The product was purified by chromatography over silica gel eluting with 20% EtOAc/hexane, to give 914 mg (81% yield) of [[1-[(4-fluorophenyl)methyl]-2-methyl-1H-indol-4-yl]oxy]acetic acid methyl ester, mp, 92–98° C.

Analyses for $C_{19}H_{18}FNO_3$:
Calculated: C, 69.71; H, 5.54; N, 4.28.
Found: C, 70.83; H, 6.00; N, 4.08.

Part D. Preparation of [[3-(2-Amino-1,2-dioxoethyl)-1-[(4-fluorophenyl)methyl]-2-methyl-1H-indol-4-yl]oxy]acetic Acid Methyl Ester Oxalyl chloride (0.24 mL, 2.6 mmol) was added to 914 mg (2.8 mmol) of [[1-[(4-fluorophenyl)methyl]-2-methyl- 1H-indol-4-yl]oxy]acetic acid methyl ester in 15 mL of methylene chloride and the mixture stirred for 1.3 hour. The mixture was concentrated at reduced pressure, the residue redissolved in 15 mL of methylene chloride and ammonia gas bubbled in for 0.25 hours, stirred for 0.25 hours and concentrated. The residue was stirred with EtOAc/water and the undissolved material filtered to give 25 mg (4% yield) of [[3-(2-amino-1,2-dioxoethyl)-1-(4-fluorophenyl)methyl]-2-methyl-1H-indol-4-yl]oxy]acetic acid methyl ester. The EtOAc layer from the filtrate was separated, washed with brine, dried ($MgSO_4$) and concentrated. The residue was chromatographed on silica gel eluting with EtOAc to give an additional 757 mg of [[3-(2-amino-1,2-dioxoethyl)-1-[(4-fluorophenyl)methyl]-2-methyl-1H-indol-4-yl]oxy]acetic acid methyl ester, mp, 178–180° C. The total combined yield of product was 70%.

Analyses for $C_{21}H_{19}FN_2O_5$:

Calculated: C, 63.31; H, 4.81; N, 7.03.

Found: C, 62.31; H, 4.78; N, 6.85.

Part E. Preparation of [[3-(2-Amino-1,2-dioxoethyl)-1-[(4-fluorophenyl)methyl]-2-methyl-1H-indol-4-yl]oxy]acetic Acid A mixture of 767 mg (1.9 mmol) of [[3-(2-amino-1,2-dioxoethyl)-1-[(4-fluorophenyl)methyl]-2-methyl-1H-indol-4-yl]oxy]acetic acid methyl ester, 10 mL of 1N NaOH and 30 mL of MeOH was heated to maintain reflux for 0.67 hours, cooled to room temperature and stirred 1 hour. Ethyl acetate and water were added and the aqueous layer separated, made acidic to pH 2–3 with 1N HCl and the mixture extracted with ethyl acetate two times. The combined ethyl acetate extracts were dried ($MgSO_4$) and concentrated. The remaining solid was washed with a small volume of ethyl acetate to give 593 mg (81% yield) of [[3-(2-amino-1,2-dioxoethyl)-1-[(4-fluorophenyl)methyl]-2-methyl-1H-indol-4-yl]oxy]acetic acid, mp, 244–247° C.

Analyses for $C_{20}H_{17}FN_2O_5$:

Calculated: C, 62.50; H, 4.46; N, 7.29.

Found: C, 62.40; H, 4.57; N, 7.00.

Example 8

Preparation of [[3-(2-Amino-1,2-dioxoethyl)-2-methyl-1-[(1-naphthalenyl)methyl]-1H-indol-4-yl]oxy]acetic Acid, a Compound Represented by the Formula

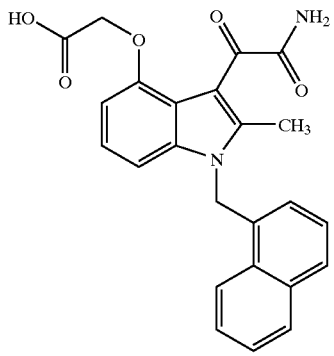

Part A. Preparation of 4-Methoxy-2-methyl-1-[(1-naphthalenyl)methyl]-1H-indole

4-Methoxy-2-methyl-1H-indole (644 mg, 4 mmol) was dissolved in 10 mL of DMF and 160 mg (4 mmol) of 60% NaH/mineral oil was added. After 0.67 hours, 707 mg (4 mmol) of 1-(chloromethyl)naphthalene was added. After 5 hours, the mixture was diluted with water and extracted twice with ethyl acetate. The combined ethyl acetate was washed with brine, dried ($MgSO_4$) and concentrated at reduced pressure. The residue was chromatographed on silica gel and eluted with 20% EtOAc/hexane to give 1.17 g (97% yield) of 4-methoxy-2-methyl-1-[(1-naphthalenyl) methyl]-1H-indole.

Analyses for $C_{21}H_{19}NO$:

Calculated: C, 83.69; H, 6.35; N, 4.65.

Found: C, 83.71; H, 6.45; N, 4.41.

Part B. Preparation of 4-Hydroxy-2-methyl-1-[(1-naphthalenyl)methyl]-1H-indole

By the method used in Example 1, Part D, 1.17 g (3.9 mmol) of 4-methoxy-2-methyl-1-[(1-naphthalenyl)methyl]-1H-indole was O-demethylated by treating it with 15.6 mL of 1M $BBr_3/CH_2Cl_2$ to give a material that was chromatographed on silica gel (eluted with 20% EtOAc/hexane then 50% EtOAc/hexane) to give 796 mg (71% yield) of 4-hydroxy-2-methyl-1-[(1-naphthalenyl)methyl]-1H-indole.

Part C. Preparation of [[2-Methyl-1-[(1-naphthalenyl)methyl]-1H-indol-4-yl]oxy]acetic Acid Methyl Ester Using the procedure described in Example 1, Part E, 4-hydroxy-2-methyl-1-[(1-naphthalenyl)methyl]-1H-indole (796 mg, 2.8 mmol) was treated with 112 mg (2.8 mmol) of 60% NaH/mineral oil and then 0.27 mL (0.27 mmol) of methyl bromoacetate. The product was purified by chromatography over silica gel eluting with 20% EtOAc/hexane to give 450 mg (45% yield) of [[2-methyl-1-[(1-naphthalenyl) methyl]-1H-indol-4-yl]oxy]acetic acid methyl ester, 167–171° C.

Analyses for $C_{23}H_{21}NO_3$:

Calculated: C, 76.86; H, 5.89; N, 3.90.

Found: C, 77.95; H, 6.25; N, 3.72.

Part D. Preparation of [[3-(2-Amino-1,2-dioxoethyl)-2-methyl-1-[(1-naphthalenyl)methyl)-1H-indol-4-yl]oxy]acetic Acid Methyl Ester Using the procedure in Example 1, Part F, 445 g (1.24 mmol) of [[2-methyl-1-[(1-naphthalenyl)methyl]-1H-indol-4-yl]oxy]acetic acid methyl ester was reacted first with 0.11 mL (1.24 mmol) of oxalyl chloride and then excess ammonia to give a white solid. This was stirred with ethyl acetate and water. The EtOAc was washed with brine, dried ($MgSO_4$) and concentrated at reduced pressure. The residue was chromatographed on silica gel eluting with ethyl acetate to give 409 mg of [[3-(2-amino-1,2-dioxoethyl)-2-methyl-1-[(1-naphthalenyl)methyl)-1H-indol-4-yl]oxy]acetic acid methyl ester, mp 188–190° C.

Analyses for $C_{25}H_{22}N_2O_5$:

Calculated: C, 69,76; H, 5.15; N, 6.51.

Found: C, 69.94; H, 5.28; N, 6.55.

Part E. Preparation of [[3-(2-Amino-1,2-dioxoethyl)-2-methyl-1-[(1-naphthalenyl)methyl)-1H-indol-4-yl]oxy]acetic Acid A mixture of 402 mg (0.93 mmol) of [[3-(2-amino-1,2-dioxoethyl)-2-methyl-1-[(1-naphthalenyl)methyl)-1H-indol-4-yl]oxy]acetic acid, 5 mL of 1N NaOH and 15 mL of MeOH was heated to maintain reflux for 0.5 hours, stirred at room temperature for 0.5 h and concentrated at reduced pressure. The residue was taken up in ethyl acetate and water, the aqueous layer separated and made acidic to pH 2–3 with 1N HCl. The mixture was extracted with ethyl acetate, the ethyl acetate was washed with brine, dried (MgSO$_4$), and concentrated at reduced pressure. The residue was stirred with ether/methylene chloride and filtered to give 284 mg (73% yield) of [[3-(2-amino-1,2-dioxoethyl)-2-methyl-1-[(1-naphthalenyl)methyl]-1H-indol-4-yl]oxy] acetic acid, mp, 233–235° C.

Analyses for $C_{24}H_{20}N_2O_5$:

Calculated: C, 69.22; H, 4.84; N, 6.73.

Found: C, 68.98; H, 5.01; N, 6.36.

Example 9

Preparation of [[3-(2-Amino-1,2-dioxoethyl)-2-ethyl-1-(phenylmethyl)-1H-indol-4-yl]oxy]acetic Acid, a Compound Represented by the Formula

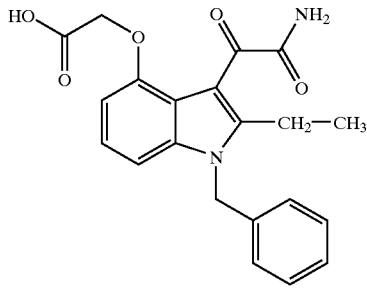

Part A. Preparation of 2-Ethyl-4-methoxy-1H-indole

A solution of 140 mL (0.18 mol) of 1.3M sec-butyl lithium in cyclohexane was added slowly to N-tert-butoxycarbonyl-3-methoxy-2-methylaniline (21.3 g, 0.09 mol) in 250 mL of THF keeping the temperature below −40° C. with a dry ice-ethanol bath. The bath was removed and the temperature allowed to rise to 0° C. and then the bath replaced. After the temperature had cooled to −60° C., 18.5 g (0.18 mol) of N-methoxy-N-methylpropanamide in an equal volume of THF was added dropwise. The reaction mixture was stirred 5 minutes, the cooling bath removed and stirred an additional 18 hours. It was then poured into a mixture of 300 mL of ether and 400 mL of 0.5N HCl. The organic layer was separated, washed with water, brine, dried over MgSO$_4$, and concentrated at reduced pressure to give 25.5 g of a crude of 1-[2-(tert-butoxycarbonylamino)-6-methoxyphenyl]-2-butanone. This material was dissolved in 250 mL of methylene chloride and 50 mL of trifluoroacetic acid and stirred for a total of 17 hours. The mixture was concentrated at reduced pressure and ethyl acetate and water added to the remaining oil. The ethyl acetate was separated, washed with brine, dried (MgSO$_4$) and concentrated The residue was chromatographed three times on silica eluting with 20% EtOAc/hexane to give 13.9 g of 2-ethyl-4-methoxy-1H-indole.

Analyses for $C_{11}H_{13}NO$:

Calculated: C, 75.40; H, 7.48; N, 7.99.

Found: C, 74.41; H, 7.64; N, 7.97.

Part B. Preparation of 2-Ethyl-4-methoxy-1-(phenylmethyl)-1H-indole

2-Ethyl4-methoxy-1H-indole (4.2 g, 24 mmol) was dissolved in 30 mL of DMF and 960 mg (24 mmol) of 60% NaH/minerial oil was added. After 1.5 hours, 2.9 mL (24 mmol) of benzyl bromide was added. After 4 hours, the mixture was diluted with water and extracted twice with ethyl acetate. The combined ethyl acetate was washed with brine, dried (MgSO$_4$) and concentrated at reduced pressure. The residue was chromatographed on silica gel and eluted with 20% EtOAc/hexane to give 3.1 g (49% yield) of 2-ethyl-4-methoxy-1-(phenylmethyl)-1H-indole.

Part C. Preparation of 2-Ethyl-4-hydroxy-1-(phenylmethyl)-1H-indole

By the method used in Example 1, Part D, 3.1 g (11.7 mmol) of 2-ethyl-4methoxy-1-(phenylmethyl)-1H-indole was O-demethylated by treating it with 48.6 mL of 1M BBr$_3$/CH$_2$Cl$_2$ to give a material that was chromatographed on silica gel (eluted with 20% EtOAc/hexane) to give 1.58 g (54% yield) of 2-ethyl-4-hydroxy-1-(phenylmethyl)-1H-indole, mp, 86–90° C.

Analyses for $C_{17}H_{17}NO$:

Calculated: C, 81.24; H, 6.82; N, 5.57.

Found: C, 81.08; H, 6.92; N, 5.41.

Part D. Preparation of [[2-Ethyl-1-(phenylmethyl)-1H-indol-4-yl]oxy]acetic Acid Methyl Ester Using the procedure described in Example 1, Part E, 2-ethyl-4-hydroxy-1-(phenylmethyl)-1H-indole (1.56 g, 6.2 mmol) was treated with 248 mg (6.2 mmol) of 60% NaH/mineral oil and then 0.6 mL (6.2 mmol) of methyl bromoacetate. The product was purified by chromatography over silica gel eluting with 20% EtOAc/hexane, to give 1.37 g (69% yield) of [[2-ethyl-1-(phenylmethyl)-1H-indol-4-yl]oxy]acetic acid methyl ester, 89–92° C.

Analyses for $C_{20}H_{21}NO_3$:

Calculated: C, 74.28; H, 6.55; N, 4.33.

Found: C, 74.03; H, 6.49; N, 4.60.

Part E. Preparation of [[3-(2-Amino-1,2-dioxoethyl)-2-ethyl-1-(phenylmethyl)-1H-indol-4-yl]oxy]acetic Acid Methyl Ester Using this procedure in Example 1, Part F, 1.36 g (4.2 mmol) of [[2-ethyl-1-(phenylmethyl)-1H-indol-4-yl]oxy] acetic acid methyl ester was reacted first with 0.4 mL (4.2 mmol) of oxalyl chloride and then excess ammonia to give a white solid. This was stirred with ethyl acetate and the insoluble material separated and dried to give 1.37 g of a mixture of [[3-(2-amino-1,2-dioxoethyl)-2-ethyl-1-(phenylmethyl)-1H-indol-4-yl]oxy]acetic acid methyl ester and ammonium chloride. This mixture melted at 172–187° C.

Part F. Preparation of [[3-(2-Amino-1,2-dioxoethyl)-2-ethyl-1-(phenylmethyl)-1H-indol-4-yl]oxy]acetic Acid A mixture of 788 mg (2 mmol) of [3-(2-amino-1,2-dioxoethyl)-2-ethyl-1-(phenylmethyl)-1H-indol-4-yl]oxy] acetic acid methyl ester, 10 mL of 1 n NaOH and 30 mL of MeOH was heated to maintain relfux for 0.5 hour, stirred at room temperature for 0.5 hour and concentrated at reduced pressure. The residue was taken up in ethyl acetate and water, the aqueous layer separated and made acidic to pH 2–3 with 1N HCl. The precipitate was filtered and washed with ethyl acetate to give 559 mg (14% yield) of [[3-(2-amino-1,2-dioxoethyl)-2-ethyl-1-(phenylmethyl)-1H-indol-4-yl]oxy]acetic acid, mp, 230–234° C.

Analyses for $C_{21}H_{20}N_2O_5$:
Calculated: C, 65.96; H, 5.80; N, 7.33.
Found: C, 66.95; H, 5.55; N, 6.99.

Example 10

Preparation of [[3-(2-Amino-1,2-dioxoethyl)-1-[(3-chlorophenyl)methyl]-2-ethyl-1H-indol-4-yl]oxy] acetic Acid, a Compound Represented by the Formula

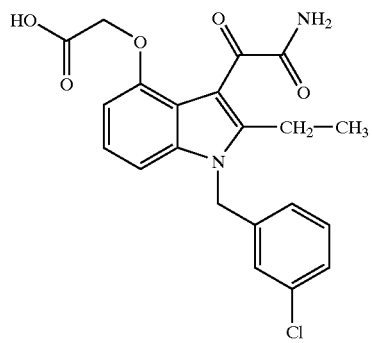

Part A. Preparation of 1-[(3-Chlorophenyl)methyl]-2-ethyl-4-methoxy-1H-indole

Using the procedure in Example 1, Part C, 1.61 g (9.2 mmol) of 2-ethyl-4-methoxy-1H-indole was reacted with 368 mg (9.2 mmol) of 60% NaH/minerial oil and then 1.2 mL (9.2 mmol) of 3-chlorobenzyl chloride in 10 mL of DMF to give a 1.34 g (49% yield) of 1-[(3-chlorophenyl)methyl]-2-ethyl-4-methoxy-1H-indole after chromatography on silica gel(eluting with 20% EtOAc/hexane).

Part B. Preparation of 1-[(3-Chlorophenyl)methyl]-2ethyl-4-hydroxy-1H-indole

By the same procedure as in Example 1, Part D, 1.34 g (4.5 mmol) of 1-[(3-chlorophenyl)methyl]-2-ethyl-4-hydroxy-1H-indole was O-demethylated using 36 mL of 1N $BBr_3$ to give after chromatography of silica gel (eluted with 5% MeOH/EtOAc 512 mg (40% yield) of 1-[(3-chlorophenyl)methyl]-2-ethyl-4-hydroxy-1H-indole.

Part C. Preparation of [[1-[(3-Chlorophenyl)methyl]-2-ethyl-1H-indol-4-yl]oxy]acetic Acid Methyl Ester Using the procedure described in Example 1, Part E, 1-[(3-chlorophenyl)methyl]-2-ethyl-4-hydroxy-1H-indole (512 mg, 1.8 mmol) was treated with 72 mg (1.8 mmol) of 60% NaH/mineral oil and then 0.17 mL (1.8 mmol) of methyl bromoacetate. The product was purified by chromatography over silica gel eluting with 20% EtOAc/hexane, to give 418 mg (65% yield) of [[1-[(3-chlorophenyl)methyl]-2-ethyl-1H-indol-4-yl]oxy]acetic acid methyl ester, mp, 85–90° C.

Analyses for $C_{20}H_{20}ClNO_3$:
Calculated: C, 67.13; H, 5.63; N, 3.91.
Found: C, 64.41; H, 5.63; N, 3.10.

Part D. [[3-(2-Amino-1,2-dioxoethyl)1-[(3-chlorophenyl)methyl]-2-ethyl-1H-indol-4-yl]oxy] acetic Acid Methyl Ester Using the procedure in Example 1, Part F, 410 mg (1.15 mmol) of [[1-[(3-chlorophenyl)methyl]-2-ethyl-1H-indol-4-yl]oxy]acetic acid methyl ester was reacted first with 0.1 mL (1.15 mmol) of oxalyl chloride and then excess ammonia to give a white solid. This solid was stirred with ethyl acetate and the insoluble material separated and dried to give 424 mg of a mixture of [[3-(2-amino-1,2-dioxoethyl)1-[(3-chlorophenyl)methyl]-2-ethyl-1H-indol-4-yl]oxy]acetic acid methyl ester and ammonium chloride. This mixture melted at 173–185° C.

Part E. Preparation of [[3-(2-Amino-1,2-dioxoethyl)1-[(3-chlorophenyl)methyl]-2-ethyl-1H-indol-4-yl] oxy]acetic Acid Using the procedure described in Example 2, Part E, 418 mg (1 mmol) of [[3-(2-amino-1,2-dioxoethyl)1-[(3-chlorophenyl)methyl]-2-ethyl-1H-indol-4-yl]oxy]acetic acid methyl ester was hydrolyzed in 5 mL of 1N NaOH and 15 mL of MeOH to give 268 mg (61% yield) of [[3-(2-amino-1,2-dioxoethyl)1-[(3-chlorophenyl)methyl]-2-ethyl-1H-indol-4-yl]oxy]acetic acid, sodium salt, mp, >265° C.

Analyses for $C_{21}H_{18}ClN_2O_5Na$:
Calculated: C, 57.74; H, 4.15; N, 6.41.
Found: C, 58.36; H, 4.61; N, 5.57.

There was also obtained 60 mg (14% yield) of [[3-(2-amino-1,2-dioxoethyl)1-[(3-chlorophenyl)methyl]-2-ethyl-1H-indol-4-yl]oxy]acetic acid, mp, 210–212° C.

Analyses for $C_{21}H_{19}ClN_2O_5$:
Calculated: C, 60.88; H, 4.61; N, 6.75.
Found: C, 60.53; H, 4.78; N, 6.59.

Example 11

Preparation of [[3-(2-Amino-1,2-dioxoethyl)-1-([1,1'-biphenyl]-2-ylmethyl)-2-ethyl-1H-indol-4-yl]oxy] acetic Acid, a Compound Represented by the Formula

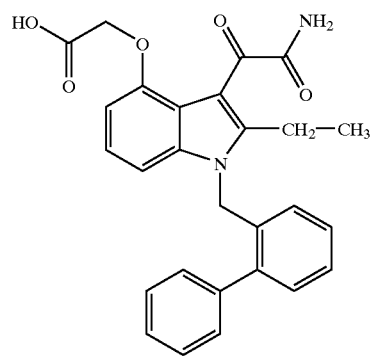

Part A. Preparation of 1-([1,1'-biphenyl]-2-ylmethyl)-2-ethyl-4-methoxy-1H-indole Using the procedure described in Example 1, Part C, 1.75 g (10 mmol) of 2-ethyl-4-methoxy-1H-indole was reacted with 400 mg (10 mmol) of 60% NaH/mineral oil and then 1.83 mL (10 mmol) of 2-(bromomethyl)biphenyl to give after chromatography on silica (eluting with 20% EtOAc/hexane) 1.25 g (37% yield) of 1-([1,1'-biphenyl]-2-ylmethyl)-2-ethyl-4-methoxy-1H-indole as an oil.

Part B. Preparation of 1-([1,1'-Biphenyl]-2-ylmethyl)-2-ethyl-4-hydroxy-1H-indole By the method used in Example 1, Part D, 911 mg (2.6 mmol) of 1-([1,1'-biphenyl]-2-ylmethyl)-2-ethyl-4- methoxy-1H-indole was O-demethylated by treating it with 10 mL of 1M BBr$_3$/CH$_2$Cl$_2$. The crude product was chromatographed on silica gel and eluted with 20% EtOAc/hexane to give 590 mg (69% yield) of 1-([1,1'-biphenyl]-2-ylmethyl)-2-ethyl-4-hydroxy-1H-indole as an oil.

Part C. Preparation of [[1-([1,1'-Biphenyl]-2-ylmethyl)-2-ethyl-1H-indol-4-yl]oxy]acetic Acid Methyl Ester 1-([1,1'-Biphenyl]-2-ylmethyl)-2-ethyl-4-hydroxy-1H-indole (911 mg, 2.8 mmol) was alkylated by treating with 0.26 mL (2.8 mmol) of methyl bromoacetate and 111 mg (2.8 mmol) of 60% NaH/minerial oil in DMF as described in Example 1, Part E. The product was purified by chromatography over silica gel eluting with 20% EtOAc/hexane, to give 655 mg (59% yield) of [[1-([1,1'-biphenyl]-2-ylmethyl)-2-ethyl-1H-indol-4-yl]oxy]acetic acid methyl ester.

Part D. Preparation of [[3-(2-Amino-1,2-dioxoethyl)-1-([1,1'-biphenyl]-2-ylmethyl)-2-ethyl-1H-indol-4-yl]oxy]acetic Acid Methyl Ester Oxalyl chloride (0.12 mL, 1.4 mmol) was added to 555 mg (1.4 mmol) of [[1-([1,1'-biphenyl]-2-ylmethyl)-2-ethyl-1H-indol-4-yl]oxy]acetic acid methyl ester in 10 mL of methylene chloride and the mixture stirred for 2.5 hours at room temperature. The mixture was concentrated at reduced pressure, the residue redissolved in 10 mL of methylene chloride, anhydrous ammonia bubbled in for 0.25 hours and the precipitate filtered. This precipitate was chromatographed on silica gel and eluted with EtOAc to give 605 mg (92% yield) of [[3-(2-amino-1,2-dioxoethyl)-1-([1,1'-biphenyl]-2-ylmethyl)-2-ethyl-1H-indol-4-yl]oxy]acetic acid methyl ester.

Part E. Preparation of [[3-(2-Amino-1,2-dioxoethyl)-1-([1,1'-biphenyl]-2-ylmethyl)-2-ethyl-1H-indol-4-yl]oxy]acetic Acid A mixture of 600 mg (1.3 mmol) of [[3-(2-amino-1,2-dioxoethyl)-1-([1,1'-biphenyl]-2-ylmethyl)-2-ethyl-1H-indol-4-yl]oxy]acetic acid methyl ester in 8 mL of 1N NaOH and 20 mL of MeOH was heated to maintain reflux for 0.67 hours, concentrated at reduced pressure and the residue taken up in EtOAc/water. The aqueous layer was separated, made acidic with 1N HCl and extracted with EtOAc. The EtOAc solution was dried (MgSO$_4$) and evaporated and the residue crystallized from MeOH to give 352 mg (59% yield) of [[3-(2-amino-1,2-dioxoethyl)-1-([1,1'-biphenyl]-2-ylmethyl)-2-ethyl-1H-indol-4-yl]oxy]acetic acid, mp, 211–214° C.

Analyses for C$_{27}$H$_{24}$N$_2$O$_5$:

Calculated: C, 71.04; H, 5.30; N, 6.14.

Found: C, 71.26; H, 5.54; N, 5.98.

Example 12

Preparation of [[3-(2-amino-1,2-dioxoethyl)-1-([1,1'-biphenyl]-2-ylmethyl)-2-propyl-1H-indol-4-yl]oxy]acetic Acid, a Compound Represented by the Formula

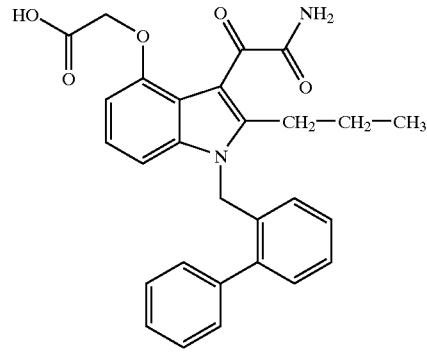

Part A. Preparation of 4-Methoxy-2-propyl-1H-indole

A solution of 50 mL (65 mmol) of 1.3M sec-butyl lithium in cyclohexane was added slowly to N-tert-butoxycarbonyl-3-methoxy-2-methylaniline (7.7 g, 32.5 mmol) in 100 mL of THF keeping the temperature below −40° C. with a dry ice-ethanol bath. The bath was removed and the temperature allowed to rise to −10° C. and then the bath replaced. After the temperature said cooled to −60° C., 4.3 g (32.5 mmol) of N-methoxy-N-methylbutanamide in an equal volume of THF was added dropwise. The reaction mixture was stirred 1 hour, the cooling bath removed and stirred an additional 22 hours. It was then poured into a mixture of 200 mL of ether and 200 mL of 0.5N HCl. The organic layer was separated, washed with brine, dried over MgSO$_4$, and concentrated at reduced pressure to give 9.9 g of crude 1-[2-(tert-butoxycarbonylamino)-6-methoxyphenyl]-2-pentanone. This material was dissolved in 100 mL of methylene chloride and 20 mL of trifluoroacetic acid and stirred for a total of 23 hours. The mixture was washed with water, dried (MgSO$_4$) and concentrated at reduced pressure. The residue was chromatographed on silica gel eluting with 20% EtOAc/hexane to give 2.19 g of 4-methoxy-2-propyl-1H-indole as an oil.

Analysis for C$_{12}$H$_{15}$NO:

Calculated: C, 76.16; H, 7.99; N, 7.40.

Found: C, 74.18; H, 8.10; N, 6.51.

Part B. Preparation of 1-([1,1-biphenyl]-2-ylmethyl)-4-methoxy-2-propyl-1H-indole Using the procedure described in Example 1, Part C, 945 mg (5 mmol) of 4-methoxy-2-propyl-1H-indole was reacted with 200 mg (5 mmol) of 60% NaH/mineral oil and then 0.92 mL (5 mmol) of 2-(bromomethyl)biphenyl to give after chromatography on silica gel (eluting with 20% EtOAc/hexane) 1.16 g (65% yield) of 1-([1'-biphenyl]-2-ylmethyl)-4-methoxy-2-propyl-1H-indole as an oil.

Part C. Preparation of 1-([1,1'-Biphenyl]-2-ylmethyl)-4-hydroxy-2-propyl-1H-indole By the method used in Example 1, Part D, 1.16 g (3.27 mmol) of 1-([1,1'-biphenyl]-2-ylmethyl)-4-methoxy-2-propyl-1H-indole was O-demethylated by treating it with 13 mL of 1M BBr₃/CH₂Cl₂. The crude product was chromatographed on silica gel and eluted with 20% EtOAc/hexane to give 794 mg (71% yield) of 1-([1,1'-biphenyl]-2-ylmethyl)-4-hydroxy-2-propyl-1H-indole as an oil.

Part D. Preparation of [[1-([1,1'-Biphenyl]-2-ylmethyl)-2-propyl-1H-indol-4-yl]oxy]acetic Acid Methyl Ester 1-([1,1'- Biphenyl]-2-ylmethyl)-4-hydroxy-2-propyl-1H-indole (794 mg, 2.8 mmol) was alkylated by treating with 0.22 mL (2.3 mmol) of methyl bromoacetate and 93 mg (2.3 mmol) of 60% NaH/mineral oil in DMF as described in Example 1, Part E. The product was purified by chromatography over silica gel eluting with 20% EtOAc/hexane, to give 533 mg (56% yield) of [[1-([1,1'-biphenyl]-2-ylmethyl)-2-propyl-1H-indol-4-yl]oxy]acetic acid methyl ester.

Part E. Preparation of [[3-(2-Amino-1,2-dioxoethyl)-1-([1,1'-biphenyl 1]-2-ylmethyl)-2-propyl-1H-indol-4-yl]oxy]acetic Acid Methyl Ester Oxalyl chloride (0.11 mL, 1.3 mmol) was added to 533 mg (1.3 mmol) of [[1-([1,1'-biphenyl]-2-ylmethyl)-2-propyl-1H-indol-4-yl]oxy]acetic acid methyl ester in 10 mL of methylene chloride and the mixture stirred for 2.0 hours at room temperature. The mixture was concentrated at reduced pressure, the residue redissolved in 10 mL of methylene chloride, anhydrous ammonia bubbled in for 0.25 hours and the mixture concentrated at reduced pressure. The residue was taken up in EtOAc/water, the EtOAc separated, washed with brine and dried (MgSO₄). After concentrating, the residue was chromatographed on silica and eluted with EtOAc to give 440 mg (70% yield) of [[3-(2-amino-1,2-dioxoethyl)-1-([1,1'-biphenyl]-2-ylmethyl)-2-propyl-1H-indol-4-yl]oxy]acetic acid methyl ester.

Part F. Preparation of [[3-(2-Amino-1,2-dioxoethyl)-1-([1,1'-biphenyl)-2-ylmethyl)-2-propyl-1H-indol-4-yl]oxy]acetic Acid A mixture of 440 mg (0.9 mmol) of [[3-(2-amino-1,2-dioxoethyl)-1-([1,1'-biphenyl]-2-ylmethyl)-2-propyl-1H-indol-4-yl]oxy]acetic acid methyl ester in 5 mL of 1N NaOH and 15 mL of MeOH was stirred for 0.75 hours, concentrated at reduced pressure and the residue taken up in EtOAc/water. The aqueous layer was separated, made acidic with 1N HCl to pH 2–3 and extracted with EtOAc. The EtOAc solution was dried (MgSO₄) and evaporated to give 374 mg (88% yield) of [[3-(2-amino-1,2-dioxoethyl)-1-([1,1'-biphenyl]-2-ylmethyl)-2-propyl-1H-indol-4-yl]oxy] acetic acid.

Analyses for $C_{28}H_{26}N_2O_5$:

Calculated: C, 71.47; H, 5.57; N, 5.95.

Found: C, 69.58; H, 5.65; N, 5.53.

Example 13

Preparation of [[3-(2-Amino-1,2-dioxoethyl)-2-cyclopropyl-1-(phenylmethyl)-1H-indol-4-yl]oxy] acetic Acid, a Compound Represented by the Formula

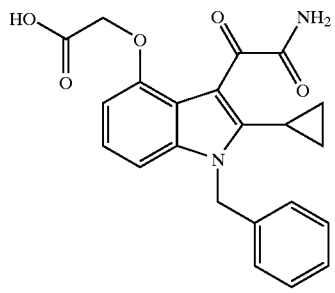

Part A. Preparation of 2-Cyclopropyl-4-methoxy-1H-indole

Using the procedure described in Example 9, Part A, 100 mL (130 mmol) of 1.3M sec-butyl lithium in cyclohexane was reacted with N-tert-butoxycarbonyl-3-methoxy-2-methylaniline (15.4 g, 65 mmol) in 100 mL of THF and then with 8.4 g (65 mmol) of N-methoxy-N-methylcyclopropylcarboxamide to give crude [2-(tert-butoxycarbonylamino)-6-methoxyphenyl]methyl cyclopropyl ketone. This material on treatment with 20 mL of trifluoroacetic acid in 300 mL of methylene chloride for 6 hours gave a material that was chromatographed on silica gel. Eluting with a gradient, toluene∅5% EtOAc/toluene, there was obtained 6.4 g (52% yield) of 2-cyclopropyl-4-methoxy-1H-indole as an oil.

Analysis for $C_{12}H_{13}NO$:

Calculated: C, 76.98; H, 7.00; N, 7.48.

Found: C, 74.33; H, 7.11; N, 6.62.

Part B. Preparation of 2-Cyclopropyl-4-methoxy-1-(phenylmethyl)-1H-indole

Using the procedure described in Example 1, Part C, 935 mg (5 mmol) of 2cyclopropoyl-4-methoxy-1H-indole was reacted with 200 mg (5 mmol) of 60% NaH/mineral oil and then 0.6 mL (5 mmol) of benzyl bromide to give after chromatography on silica gel (eluting with 20% EtOAc/hexane) 630 mg (45% yield) of 2-cyclopropyl-4-methoxy-1-(phenylmethyl)-1H-indole as an oil.

Part C. Preparation of 2-Cyclopropyl-4-hydroxy-1-(phenylmethyl)-1H-indole

By the method used in Example 1, Part D, 630 g (2.3 mmol) of 2-cyclopropyl-4-methoxy-1-(phenylmethyl)-1H-indole was O-demethylated by treating it with 9 mL of 1M BBr₃/CH₂Cl₂. The crude product was chromatographed on silica gel and eluted with 20% EtOAc/hexane to give 316 mg (52% yield) of 2-cyclopropyl-4-hydroxy-1-(phenylmethyl)-1H-indole as an oil.

Part D. Preparation of [[2-Cyclopropyl-1-(phenylmethyl)-1H-indol-4-yl]oxy]acetic Acid Methyl Ester 2-Cyclopropyl-4-hydroxy-1-(phenylmethyl)-1H-indole (316 mg, 1.2 mmol) was alkylated by treating with 0.11 mL (1.2 mmol) of methyl bromoacetate and 48 mg (1.2 mmol)

of 60% NaH/mineral oil in DMF as described in Example 1, Part E. The product was purified by chromatography over silica gel eluting with 20% EtOAc/hexane, to give 253 mg (63% yield) of [[2-cyclopropyl-1-(phenylmethyl)-1H-indol-4-yl]oxy]acetic acid methyl ester.

Part E. Preparation of [[3-(2-Amino-1,2-dioxoethyl)-2-cyclopropyl-1-(phenylmethyl)-1H-indol-4-yl]oxy]acetic Acid Methyl Ester Oxalyl chloride (0.07 mL, 0.76 mmol) was added to 253 mg (0.76 mmol) of [[2-cyclopropyl-1-(phenylmethyl)-1H-indol-4-yl]oxy]acetic acid methyl ester in 10 mL of methylene chloride and the mixture stirred for 1.5 hours at room temperature. The mixture was concentrated at reduced pressure, the residue redissolved in 10 mL of methylene chloride, anhydrous ammonia bubbled in for 0.25 hours. A precipitate formed and was separated to give 226 mg of a mixture of [[3-(2-amino-1,2-dioxoethyl)-2-cyclopropyl-1-(phenylmethyl)-1H-indol-4-yl]oxy]acetic acid methyl ester and ammonium chloride.

Part F. Preparation of [[3-(2-Amino-1,2-dioxoethyl)-2-cyclopropyl-1-(phenylmethyl)-1H-indol-4-yl]oxy]acetic Acid A mixture of 220 mg (0.54 mmol) of [[3-(2-amino-1,2-dioxoethyl)-2-cyclopropyl-1-(phenylmethyl)-1H-indol-4-yl]oxy]acetic acid methyl ester in 5 mL of 1N NaOH and 15 mL of MeOH was heated to maintain reflux for 0.67 hours, concentrated at reduced pressure and the residue taken up in EtOAc/water. The aqueous layer was separated, made acidic with 1N HCl to pH 2–3 and EtOAc added. A precipitate formed and was separated to give 169 mg (80% yield) of [[3-(2-amino-1,2-dioxoethyl)-2-cyclopropyl-1-(phenylmethyl)-1H-indol-4-yl]oxy]acetic acid, mp, 246–249° C.

Analyses for $C_{22}H_{20}N_2O_5$:

Calculated: C, 67.34; H, 5.14; N, 7.14.

Found: C, 67.11; H, 5.33; N, 6.86.

Example 14

Preparation of [[3-(2-Amino-1,2-dioxoethyl)-1-([1,1'-biphenyl]-2-ylmethyl)-2-cyclopropyl-1H-indol-4-yl]oxy]acetic Acid, a Compound Represented by the Formula

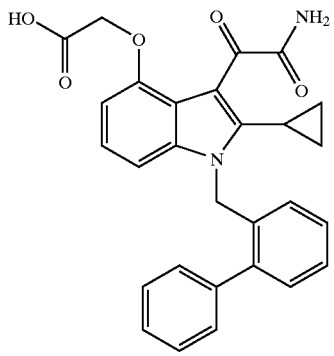

Part A. Preparation of 1-([1,1'-Biphenyl]-2-ylmethyl)-2-cyclopropyl-4-methoxy-1H-indole Using the procedure described in Example 1, Part C, 935 mg (5 mmol) of 2-cyclopropyl-4-methoxy-1H-indole was reacted with 200 mg (5 mmol) of 60% NaH/mineral oil and then 0.92 mL (5 mmol) of 2-(bromomethyl)biphenyl to give after chromatography on silica gel (eluting with 20% EtOAc/hexane) 911 mg (52% yield) of 1-([1,1'-biphenyl]-2-ylmethyl)-2-cyclopropyl-4-methoxy-1H-indole as an oil.

Part B. Preparation of 1-([1,1'-Biphenyl]-2-ylmethyl)-2-cyclopropyl-4-hydroxy-1H-indole By the method used in Example 1, Part D, 1.25 g (3.7 mmol) of 1-([1,1'-biphenyl]-2-ylmethyl)-2-cyclopropyl-4-methoxyl-1H-indole was O-demethylated by treating it with 15 mL of 1M $BBr_3/CH_2Cl_2$. The crude product was chromatographed on silica gel and eluted with 20% EtOAc/hexane to give 367 mg (29% yield) of 1-([1,1'-biphenyl]-2-ylmethyl)-2-cyclopropyl-4-hydroxy-1H-indole as an oil.

Part C. Preparation of [[1-([1,1'-Biphenyl]-2-ylmethyl)-2-cyclopropyl]-1H-indol-4-yl]oxy]acetic Acid Methyl Ester 1-([1,1'-Biphenyl]-2-ylmethyl)-2-cyclopropyl-4-hydroxy-1H-indole (367 mg, 1.1 mmol) was alkylated by treating with 0.1 mL (1.1 mmol) of methyl bromoacetate and 43 mg (1.1 mmol) of 60% NaH/mineral oil in DMF as described in Example 1, Part E. The product was purified by chromatography over silica gel eluting with 20% EtOAc/hexane to give 265 mg (59% yield) of [[11-([1,1'-biphenyl]-2-ylmethyl)-2-cyclopropyl-1H-indol-4-yl]oxy]acetic acid methyl ester.

Part D. Preparation of [[3-(2-Amino-1,2-dioxoethyl)-1-([1,1'-biphenyl]-2-ylmethyl)-2-cyclopropyl-1H-indol-4-yl]oxy]acetic Acid Methyl Ester Oxalyl chloride (0.06 mL, 0.64mmol) was added to 265 mg (0.64 mmol) of [[1-([1,1'-biphenyl]-2-ylmethyl)-2-cyclopropyl-1H-indol-4-yl]oxy]acetic acid methyl ester in 10 mL of methylene chloride and the mixture stirred for 1.5 hours at room temperature. The mixture was concentrated at reduced pressure, the residue redissolved in 10 mL of methylene chloride, anhydrous ammonia bubbled in for 0.25 hours and the mixture concentrated at reduced pressure. The residue was taken up in EtOAc/water, the EtOAc separated, washed with brine and dried ($MgSO_4$). After concentrating, the residue was chromatographed on silica and eluted with EtOAc to give 181 mg (59% yield) of [[3-(2-amino-1,2-dioxoethyl)-1-([1,1'-biphenyl]-2-ylmethyl)-2-cyclopropyl-1H-indol-4-yl]oxy]acetic Acid Methyl Ester

Part E. Preparation of [[3-(2-Amino-1,2-dioxoethyl)-1-([1,1'-biphenyl]-2-ylmethyl)-2-cyclopropyl-1H-indol-4-yl]oxy]acetic Acid A mixture of 175 mg (0.36 mmol) of [[3-(2-amino-1,2-dioxoethyl)-1-([1,1'-biphenyl]-2-ylmethyl)-2-cyclopropyl-1H-indol-4-yl]oxy]acetic acid methyl ester in 4 mL of 1N NaOH and 10 mL of MeOH was stirred for 0.5 hours, concentrated at reduced pressure and the residue taken up in EtOAc/water. The aqueous layer was separated, made acidic with 1N HCl to pH 2–3 and extracted with EtOAc. The EtOAc solution was dried ($MgSO_4$), evaporated and the residue stirred with EtOAc/ether. The insoluble material was filtered to give 105 mg (62% yield) of [[3-(2-amino-1,2-dioxoethyl)-1-([1,1'-biphenyl]-2-ylmethyl)-2-cyclopropyl-1H-indol-4-yl]oxy]acetic acid, mp, 172–174° C.

Analyses for $C_{28}H_{24}N_2O_5$:
Calculated: C, 71.78; H, 5.16; N, 5.98.
Found: C, 72.08; H, 5.30; N, 5.92.

Example 15

Preparation of 4-[[3-(2-Amino-1,2-dioxoethyl)-2-ethyl-1-(phenylmethyl))-1H-indol-5-yl]oxy]butanoic Acid, a Compound Represented by the Formula

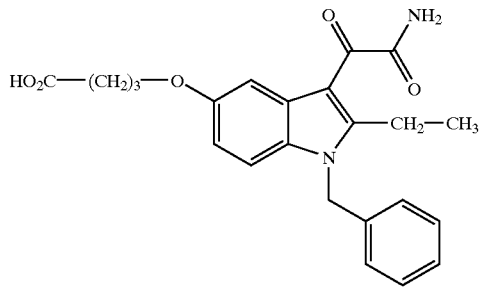

Part A. Preparation of N-tert-Butoxycarbonyl-4-methoxy-2-methylaniline

By the procedure in Example 1, Part A, 13.7 g (0.1 mole) of 4-methoxy 2-methylaniline was reacted with 25 g (0.1145 mol) of di-tert-butyl dicarbonate to give 17.25 g (73% yield) of N-tert-butoxycarbonyl-4-methoxy-2-methylaniline melting at 80–82° C., after crystallizing from hexane.

Analyses for $C_{13}H_{19}NO_3$:
Calculated: C, 65.80; H, 8.07; N, 5.90.
Found: C, 65.86; H, 8.15; N, 5.61.

Part B. Preparation of 1-[2-(tert-Butoxycarbonylamino)-5-methoxyphenyl]-2-butanone A solution of 1.3M sec-butyl lithium/cyclohexane (81 mL, 0.105 mol) was added slowly to 11.85 g (0.05 mol) of N-tert-butoxycarbonyl-4-methoxy-2-methylaniline in 80 mL of THF while keeping the temperature below −40° C. with a dry ice-ethanol bath. The bath was removed and the temperature allowed to rise to −20° C. and then the bath was replaced. After the temperature had cooled to −60° C., 6.1 g (0.052 mol) of N-methoxy-N-methylpropanamide in an equal volume of THF was added dropwise. The reaction mixture was stirred 1 hour, the cooling bath removed and stirred an additional 1 hour. It was then poured into a mixture of 200 mL of ether and 200 mL of 1N HCl. The organic layer was separated, washed with water, dried over $Na_2SO_4$ and concentrated at reduced pressure to give 10.9 g (74% yield) of 1-(2-(tert-butoxycarbonylamino)-5-methoxyphenyl]-2-butanone, melting at 80–81° C., after chromatography on silica eluting with 5% EtOAc/toluene.

Analyses for $C_{16}H_{23}NO_4$:
Calculated: C, 65.51; H, 7.90; N, 4.77.
Found: C, 65.69; H, 7.89; N, 4.90.

Part C. Preparation of 2-Ethyl-5-methoxy-1H-indole

1-[2-(tert-Butoxycarbonylamino)-5-methoxyphenyl]-2-butanone (7.33 g, 0.025 mol) in 120 mL of $CH_2Cl_2$ and 20 mL of trifluoroacetic acid was stirred for 20 hours, washed with water, $NaHCO_3$ solution and the product chromatographed on silica (eluted with 20% EtOAc/hexane) to give 2.54 g (58% yield) of 2-ethyl-5-methoxy-1H-indole as a white solid, mp 49–50° C.

Analyses for $C_{11}H_{13}NO$:
Calculated: C, 75.40; H, 7.48; N, 7.99.
Found: C, 75.64; H, 7.61; N, 8.04.

Part D. Preparation of 2-Ethyl-5-methoxy-1-(phenylmethyl)-1H-indole

2-Ethyl-5-methoxy-1H-indole (5.6 g, 21.5 mmol) was dissolved in 150 mL of DMF and 20 mL of THF and 1.0 g (25 mmol) of 60% sodium hydride was added. After stirring for 0.17 hours, 3.0 ml (25 mmol) of benzyl bromide was added. The mixture was stirred at room temperature for 10 hours, diluted with water and extracted with ethyl acetate. The ethyl acetate solution was washed with water, saturated NaCl solution, and dried ($Na_2SO_4$). The EtOAc was evaporated and the residue was chromatographed on silica gel eluting with a gradient, 5% EtOAc/hexaneØ15% EtOAc/hexane to give 4.6 g (82% yield) of 2-ethyl-5-methoxy-1-(phenylmethyl)-1H-indole.

Part E. Preparation of 2-Ethyl-5-methoxy-2-methyl-1-(phenylmethyl)-1H-indole-3-glyoxylamide Oxalyl chloride (0.8 mL, 9.2 mmol) was added to 2.1 g (7.9 mmol) of 2-ethyl-5-methoxy-1-(phenylmethyl)-1H-indole while being cooled to −5° C. The cooling bath was removed, stirring was continued for 1 hour and the mixture added at 0–5° C. to 150 mL of THF saturated with ammonia. After 0.33 hours, the mixture was diluted with water, the organic layer separated, washed with saturated NaCl solution and dried ($NaSO_4$). After concentrating at reduced pressure, the residue was chromatographed on silica gel eluting first with methylene chloride and then ether to give 2.1 g (79% yield) of 2-ethyl-5-methoxy-2-methyl-1-(phenylmethyl)-1H-indole-3-glyoxylamide.

Part F. Preparation of 2-Ethyl-5-hydroxy-2-methyl-1-(phenylmethyl)-1H-indole-3-glyoxylamide A solution of 1.3 g (4 mmol) of 2-ethyl-5-methoxy-2-methyl-1-(phenylmethyl)-1H-indole-3-glyoxylamide and 16 mL of 1M $BBr_3/CH_2Cl_2$ in 50 mL of methylene chloride was stirred for 1.5 hours, stirred with water, the organic material separated and washed with brine. After drying, the solution was concentrated at reduced pressure and the residue chromatographed on silica gel. The material was eluted with a gradient, 1% $MeOH/CH_2Cl_2$Ø3% $MeOH/CH_2Cl_2$, to give after recrystallizing from methylene chloride-ethanol 270 mg (21% yield) of 2-ethyl-5-hydroxy-2-methyl-1-(phenylmethyl)-1H-indole-3-glyoxylamide, mp 224–225° C.

Analyses for $C_{19}H_{18}N_2O_3$:
Calculated: C, 70.70; H, 5.63; N, 8.69.
Found: C, 70.99; H, 5.56; N, 8.43.

Part G. Preparation of 4-[[3-(2-Amino-1,2-dioxoethyl)-2-ethyl-1-(phenylmethyl)-1H-indol-5-yl]oxy]butanoic Acid Tert-butyl Ester 2-Ethyl-5-hydroxy-2-methyl-1-(phenylmethyl)-1H-indole-3-glyoxylamide (355 mg, 1.1 mmol) was dissolved in 10 mL of THF and 20 mL of DMF and 50 mg (1.2 mmol) of 60% NaH/mineral oil was added. After stirring for 0.17 hours, 290 mg (1.3 mmol) of tert-butyl 4-bromobutyrate was added and stirring maintained for 4.75 hours. The mixture was diluted with water, extracted with EtOAc and the EtOAc washed with water, saturated NaCl solution and dried (Na$_2$SO$_4$). After concentrating at reduced pressure, the residue was chromatographed on silica gel and eluted with a gradient, CH$_2$Cl$_2$Ø2% MeOH/CH$_2$Cl$_2$ to give after crysrtallizing from ether-hexane 460 mg (90% yield) of 4-[[3-(2-amino-1,2-dioxoethyl)-2-ethyl-1-(phenylmethyl)-1H-indol-5-yl]oxy]butanoic acid tert-butyl ester, mp 101–104° C.

Analyses for C$_{27}$H$_{32}$N$_2$O$_5$:

Calculated: C, 69.81; H, 6.94; N, 6.03.

Found: C, 70.54; H, 7.02; N, 6.37.

Part H. Preparation of 4-[[3-(2-Amino-1,2-dioxoethyl)-2-ethyl-1-(phenylmethyl)-1H-indol-5-yl]oxy]butanoic Acid A solution of 450 mg (0.97 mmol) of 4-[[3-(2-amino-1,2-dioxoethyl)-2-ethyl-1-(phenylmethyl)-1H-indol-5-yl]oxy]butanoic acid tert-butyl ester in 75 mL of methylene chloride and 1 mL of trifluoroacetic acid was stirred at room temperature for 2.25 hours and concentrated at reduced pressure. The residue was chromatographed on silica gel and eluted with EtOAc to give 250 mg (63% yield) of 4-[[3-(2-amino-1,2-dioxoethyl)-2-ethyl-1-(phenylmethyl)-1H-indol-5-yl]oxy]butanoic acid, mp 173–175° C.

Analyses for C$_{23}$H$_{24}$N$_2$O$_5$:

Calculated: C, 67.63; H, 5.92; N, 6.86.

Found: C, 67.09; H, 6.00; N, 6.76.

Example 16

Preparation of 4-[[3-(2-Amino-1,2-dioxoethyl)-1-(phenylmethyl)-H-indol-5-yl]oxy]butanoic Acid, a Compound Represented by the Formula

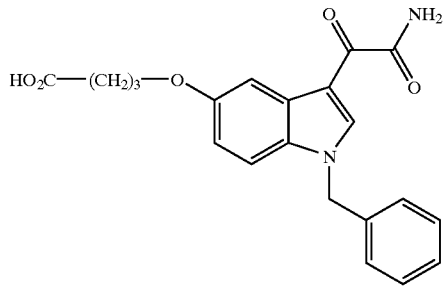

Part A. 5-Hydroxy-1-(phenylmethyl)-1H-indole

5-Methoxy-1H-indole (5.6 g, 21.5 mmol) was reacted with 1.0 g (25 mmol) of 60% sodium hydride and then 3.0 mL (25 mmol) of benzyl bromide by the method described in Example 12, Part D to give crude 5-methoxy-1-(phenylmethyl)-1H-indole. This material was dissolved in 250 mL of methylene chloride, cooled to −5° C., 50 mL of 1M BBr$_3$/CH$_2$Cl$_2$ added, the cooling bath removed and the mixture stirred for 1.75 hours. Ice water was added and the mixture stirred. The organic layer was separated, washed with saturated NaCl, dried (Na$_2$SO$_4$), and concentrated at reduced pressure. The residue was chromatographed on silica gel and eluted with 20% ether/hexaneØether to give 870 mg (19% overall yield) of crude 5-hydroxy-1-(phenylmethyl)-1H-indole.

Part B. Preparation of 4-[[1-(Phenylmethyl)-1H-indol-5-yl]oxy]butanoic Acid Ethyl Ester A solution of 850 mg (4.0 mmol) of 5-hydroxy-1-(phenylmethyl)-1H-indole in 75 mL of DMF and 20 mL of THF was treated with 200 mg (5.0 mmol) of 60% NaH/mineral oil and after stirring for 0.17 hours, 0.7 mL (4.9 mmol) of ethyl 4-bromobutyrate was added. After 2.75 hours, the mixture was diluted with water and extracted with EtOAc. The EtOAc solution was washed with water, saturated NaCl solution, dried(Na$_2$SO$_4$) and concentrated at reduced pressure. The residue was chromatographed on silica gel and the 545 mg (40% yield) of 4-[[1-(phenylmethyl)-1H-indol-5-yl]oxy]butanoic acid ethyl ester by eluting with a gradient, 15% ether/hexaneØ50% ether/hexane.

Part C. Preparation of 4-[[3-(2-Amino-1,2-dioxoethyl)-1-(phenylmethyl)-1H-indol-5-yl]oxy]butanoic Acid Ethyl Ester Oxalyl chloride (0.15 mL, 1.7 mmol) was added to 545 mg (1.6 mmol) of 4-[1-(phenylmethyl)-1H-indol-5-yl]oxy]butanoic acid ethyl ester in 40 mL of methylene chloride while cooling at −5° C. The cooling bath was removed, the mixture stirred for 0.83 hours and added to 75 mL of THF saturated with ammonia gas at 0–5° C. After 0.25 hours, the mixture was diluted with water and extracted with methylene chloride. This solution. was washed with saturated NaCl, dried (Na$_2$SO$_4$), and concentrated at reduced pressure. The residue was crystallized from methylene chloride-ethanol to give 490 mg (75% yield) of 4-[[3-(2-amino-1,2-dioxoethyl)-1-(phenylmethyl)-1H-indol-5-yl]oxy]butanoic acid ethyl ester, mp, 168–170° C.

Analyses for C$_{23}$H$_{24}$N$_2$O$_5$:

Calculated: C, 67.63; H, 5.92; N, 6.86.

Found: C, 67.60; H, 6.13; N, 6.93.

Part D. Preparation of 4-[[3-(2-Amino-1,2-dioxoethyl)-1-(phenylmethyl)-1H-indol-5-yl]oxy]butanoic Acid A mixture of 450 mg (1.1 mmol) of 4-[[3-(2-amino-1,2-dioxoethyl)-1-(phenylmethyl)-1H-indol-5-yl]oxy]butanoic acid ethyl ester in 450 mL of THF and 50 mL of 5N HCl was stirred for 16 hours, diluted with EtOAc and washed with water, saturated NaCl solution and dried (Na$_2$SO$_4$). After concentrating at reduced pressure, the residue was chromatographed on silica gel eluting first with 2% MeOH/CH$_2$Cl$_2$ and then EtOAc to give after crystallization from MeOH-CH$_2$Cl$_2$ 190 mg (45% yield) of 4-[[3-(2-amino-1,2-dioxoethyl)-1-(phenylmethyl)-1H-indol-5-yl]oxy]butanoic acid, mp, 193–195° C.

Analyses for C$_{21}$H$_{20}$N$_2$O$_5$:

Calculated: C, 66.31; H, 5.30; N, 7.36.

Found: C, 60.82; H, 5.08; N, 6.64; residue, 1.39%.

Example 17

Preparation of [[3-(Aminooxoacetyl)-2-ethyl-1-(phenylmethyl)-1H-indol-4-yl]amino]acetic Acid, a Compound Represented by the Formula

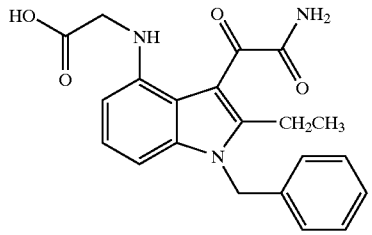

Part A. Preparation of 1-Phenylmethyl-2-ethyl-4-nitro-1H-indole

2-Ethyl -4-nitro-1H-indole (4.75 g, 25 mmol) was added to a mixture of 1.0 g (25 mmol) of 60% NaH/mineral oil (washed with hexane before adding DMF) in 40 ml DMF. After 45 minutes, 3.0 ml (25 mmol) of benzyl bromide was added. The mixture was stirred at room temperature for four hours, diluted with water, and extracted with EtOAc. The EtOAc solution was washed with brine, dried over $MgSO_4$, and evaporated in vacuo. The residue was chromatographed on silica gel eluting with 20% EtOAc/Hexane to give 6.36 g (91%) of 1-Phenylmethyl-2-ethyl-4-nitro]1H-indole as an oil.

Analyses for $C_{17}H_{16}N_2O_2$;
Calculated: C, 72.84; H, 5.75; N, 9.99.
Found: C, 72.67; H, 5.86; N, 9.69.

Part B. Preparation of 2-Ethyl-4-Nitro-α-oxo-1-(phenylmethyl)-1H-indole-3-acetamide Oxalyl chloride (1.98 ml 22.7 mmol) was added to 6.36 g (22.7 mmol) of 1-Phenylmethyl-2-ethyl-4-nitro-1H-indole in 30 ml of $CH_2Cl_2$ and the mixture stirred for 7.5 hours. Another 0.5 ml (5.7 mmol) of oxalyl chloride was then added and stirred an additional 16.5 hours. The mixture was concentrated at reduced pressure, the residue redissolved in 30 ml $CH_2Cl_2$, and $NH_3$ gas bubbled in for 0.25 hours. The mixture was evaporated in vacuo and the residue stirred with EtOAc and H2O. The EtOAc layer was washed with brine, dried over $MgSO_4$, and evaporated in vacuo. The residue was chromatographed over silica gel eluting with 20% EtOAc/Hexane to give 6.0 g (75%) of 2-Ethyl-4-Nitro-α-oxo-1-(phenylmethyl)-1H-indole-3-acetamide melting at 207–208° C.

Analyses for $C_{19}H_{17}N_3O_4$:
Calculated: C, 64.95; H, 4.88; N, 11.96.
Found: C, 65.14; H, 4.98; N, 12.11.

Part C. Preparation of 4-Amino-2-Ethyl-α-oxo-1-(phenylmethyl)-1H-indole-3-Acetamide A solution of 6.0 g (17.1 mmol) of 2-Ethyl-4-Nitro-α-oxo-1-(phenylmethyl)-1H-indole-3-acetamide in 140 ml of 1:1 THF:EtOH containing 1.0 g of 5% $Pt/BaSO_4$ was hydrogenated at room temperature and 60 psi (4.22 $Kg/cm^2$) for four hours. The catalyst was filtered and the filtrate evaporated in vacuo. The residue was chromatographed over silica gel eluting with Hexane/50 to 100% EtOAC to give 1.66 g (30%) of 4-Amino-2-Ethyl-α-oxo-1-(phenylmethyl)-1H-indole-3-Acetamide melting at 140–144° C.

Analyses for $C_{19}H_{19}N_3O_2$:
Calculated: C, 71.01; H, 5.96; N, 13.08.
Found: C, 68.50; H, 5.93; N, 11.88.

Part D. Preparation of [[3-(Aminooxoacetyl)-2-ethyl-1-(phenylmethyl)-1H-indol-4-yl]amino]acetic Acid Methyl Ester Methyl bromoacetate (0.07 ml, 0.78 mmol) was added to 250 mg (0.78 mmol) of 4-Amino-2-Ethyl-α-oxo-1-(phenylmethyl)-1H-indole-3-Acetamide in 4 ml of DMF, stirred at 60° C. for 0.5 hour, and then at room temperature for 20 hours. The mixture was diluted with water and extracted with EtOAc. The EtOAC solution was washed with brine, dried over $MgSO_4$, and evaporated in vacuo. The residue was chromatographed over silica gel eluting with Hexane/50 to 100% EtOAc to give 196 mg (64%) of [[3-(Aminooxoacetyl)-2-ethyl-1-(phenylmethyl)-1H-indol-4-yl]amino]acetic acid methyl ester melting at 188–193° C.

Analyses for $C_{22}H_{23}N_3O_4$:
Calculated: C, 67.16; H, 5.89; N, 10.68.
Found: C, 67.66; N, 5.71; N, 9.78.

Part E. Preparation of [[3-(Aminooxoacetyl)-2-ethyl-1-(phenylmethyl)-1H-indol-4-yl]amino]acetic Acid A mixture of 190 mg (0.48 mmol) of [[3-(Aminooxoacetyl)-2-ethyl-1-(phenylmethyl)-1H-indol-4-yl]amino]acetic acid methyl ester, 5 ml of 1N NaOH, and 15 ml of MeOH was refluxed 0.33 hour, cooled, and stirred at room temperature for 1 hour. EtOAc and acqueous HCl were added and the EtOAc layer was washed with brine, dried over $MgSO_4$, and evaporated in vacuo. The residue was crystallized from MeOH to give 96 mg (53%) of ([3-(Aminooxoacetyl)-2-ethyl-1-(phenylmethyl)-1H-indol-4-yl]amino]ac(e,tic acid melting at 151–157° C.

Analyses for $C_{21}H_2N_3O_4$:
Calculated: C, 66.48; H, 5.58; N, 11.08.
Found: C, 66.30; H, 5.61; N, 10.80.

Assay Experiments

Assay Example 1

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable formula Microtiter plate Reader", by Laure J. Reynolds, Lori L. Hughes, and Edward A Dennis, *Analytical Biochemistry* 204, pp. 190–197, 1992 (the disclosure of which is incorporated herein by reference):
Reagents:

| REACTION BUFFER | |
|---|---|
| CaCl2.2H2O | (1.47 g/L) |
| KCl | (7.455 g/L) |
| Bovine Serum Albumin (fatty acid free) | (1 g/L) |

-continued (Sigma A-7030, product of Sigma Chemical Co. St. Louis MO, U.S.A.)
TRIS HCl (3.94 g/L)
pH 7.5 (adjust with NaOH)
ENZYME BUFFER 0.05 NaOAc.3H2O, pH 4.5
0.2 NaCl Adjust pH to 4.5 with acetic acid DTNB—5,5'-dithiobis-2-nitrobenzoic acid RACEMIC DIHEPTANOYL THIO—PC
  racemic 1,2-bis(heptanoylthio)-1,2-dideoxy-sn-glycero-3-phosphorylcholine
  TRITON X-100™ prepare at 6.249 mg/ml in reaction buffer to equal 10 uM.

REACTION MIXTURE
  A measured volume of racemic dipheptanoyl thio PC supplied in chloroform at a concentration of 100 mg/ml is taken to dryness and redissolved in 10 millimolar TRITON X-100™ nonionic detergent aqueous solution.
  Reaction Buffer is added to the solution, then DTNB to give the Reaction Mixture.
  The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure:
1. Add 0.2 ml reaction mixture to all wells;
2. Add 10 ul test compound (or solvent blank) to appropriate wells, mix 20 seconds;
3. Add 50 nanograms of sPLA$_2$ (10 microliters) to appropriate wells;
4. Incubate plate at 40° C. for 30 minutes;
5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, IC$_{50}$ values were determined. Typically, the IC$_{50}$ values (see, Table I, below) were determined by diluting test compound serially twofold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of IC$_{50}$ values. IC$_{50}$ were determined by plotting log concentration versus inhibition values in the range from 10–90% inhibition.

Results of Human Secreted Phospholipase A$_2$ Inhibition Tests for 1H-indole-3-glyoxylamides

TABLE I

| Compound of Example No. | Inhibition of human secreted PLA$_2$ IC50 ± mean deviation (3–4 tests) |
|---|---|
| 1 | 10.67 ± 5.51 nM |
| 2 | 9.00 ± 1.73 nM |
| 3 | 5.33 ± 1.15 nM |
| 4 | 9.69 ± 1.14 nM |
| 5 | 49.00 ± 11.53 nM |
| 6 | 6.00 ± 1.00 nM |
| 7 | 6.00 ± 1.00 nM |
| 8 | 32.75 ± 7.04 nM |
| 9 | 9.00 ± 1.73 nM |
| 10 | 6.67 ± 2.89 nM |
| 11 | 4.33 ± 2.31 nM |
| 12 | 82.23 ± 18.01 nM |
| 13 | 27.60 ± 13.07 nM |
| 14 | 5.57 ± 2.89 nM |
| 15 | 210 ± 60 nM |
| 16 | 62,010 ± 3750 nM |
| 17 | 1148 ± 120 nM |

The compounds of Examples 1 to 15 are highly active in inhibiting sPLA$_2$. The compound of Example 16 (having its acidic substituent in the 5 position together with having the non-preferred hydrogen at the 2 position of the indole nucleus viz., R$_2$ in formula I) is much less active.

Assay Example 2

Method

Male Hartley strain guinea pigs (500–700 g) were killed by cervical dislocation and their heart and lungs removed intact and placed in aerated (95% O$_2$:5% CO$_2$) Krebs buffer. Dorsal pleural strips (4×1×25 mm) were dissected from intact parenchymal segments (8×4×25 mm) cut parallel to the outer edge of the lower lung lobes. Two adjacent pleural strips, obtained from a single lobe and representing a single tissue sample, were tied at either end and independently attached to a metal support rod. One rod was attached to a Grass force-displacement transducer (Model FTO3C, product of Grass Medical Instruments Co., Quincy, Mass., USA). Changes in isometric tension were displayed on a monitor and thermal *recorder (product of Modular Instruments, Malvern, Pa.). All tissues were placed in 10 ml jacketed tissue baths maintained at 37° C. The tissue baths were continuously aerated and contained a modified Krebs solution of the following composition (millimolar) NaCl, 118.2; KCl, 4.6; CaCl$_2$.2H$_2$O, 2.5; MgSO$_4$.7H$_2$O, 1.2; NaHCO$_3$, 24.8; KH$_2$PO$_4$, 1.0; and dextrose 10.0. Pleural strips from the opposite lobes of the lung were used for paired experiments. Preliminary data generated from tension/response curves demonstrated that resting tension of 800 mg was optimal. The tissues were allowed to equilibrate for 45 min. as the bath fluid was changed periodically.

Cumulative Concentration-response Curves

Initially tissues were challenged 3 times with KCl (40 mM) to test tissue viability and to obtain a consistent response. After recording the maximal response to KCl, the tissues were washed and allowed to return to baseline before the next challenge. Cumulative concentration-response curves were obtained from pleural strips by increasing the agonist concentration (sPLA$_2$) in the tissue bath by half-log$_{10}$ increments while the previous concentration remained in contact with the tissues (Ref.1, supra.) Agonist concentration was increased after reaching the plateau of the contraction elicited by the preceding concentration. One concentration-response curve was obtained from each tissue. To minimize variability between tissues obtained from different animals, contractile responses were expressed as a percentage of the maximal response obtained with the final KCl challenge. When studying the effects of various drugs on the contractile effects of sPLA$_2$, the compounds and their respective vehicles were added to the tissues 30 min. prior to star ting the sPLA$_2$ concentration-response curves.

Statistical Analysis

Data from different experiments were pooled and presented as a percentage of the maximal KCl responses (mean±S.E.). To estimate the drug induced rightward shifts in the concentration response curves, the curves were analyzed simultaneously using statistical nonlinear modeling methods similar to those described by Waud (1976), Equation 26, p. 163, (Ref.2) The model includes four parameters: the maximum tissue response which was assumed the same for each curve, the ED$_{50}$ for the control curve, the steepness of the curves, and the pA$_2$, the concentration of antagonist that requires a two-fold increase in agonist to achieve an equivalent response. The Schild slope was determined to be 1, using staistical nonlinear modeling methods similar to those described by Waud (1976), Equation 27, p. 164 (Ref. 2). The Schild slope equal to 1 indicates the model is consistent with the assumptions of a competitive antagonist; therefore, the pA$_2$ may be interpreted as the apparent K$_B$, the dissociation constant of the inhibitor.

To estimate the drug-induced suppression of the maximal responses, siPLA$_2$ responses (10 ug/ml) were determined in the absence and presence of drug, and percent suppression was calculated for each pair of tissues. Representative examples of inhibitory activities are presented in Table 2, below.

Ref. 1—van, J. M.: Cumulative dose-response curves. II. Technique for the making of dose-response curves in isolated organs and the evaluation of drug parameters. *Arch. Int. Pharmacodyne. Ther.,* 143: 299–330, 1963.

Ref. 2—Waud, D.: Analysis of dose-response relationships. in *Advances in General and Cellular Pharmacology* eds Narahashi, Bianchi 1:145–178, 1976.

Results of Human Secreted Phospholipase A$_2$ Inhibition Tests on Guinea Pig Lung Tissue

TABLE II

| Compound of Example No. | Tissue test secreted PLA$_2$ Apparent K$_B$ nM |
| --- | --- |
| 1 | 143 ± 67 |
| 3 (Na salt) | 67.6 ± 11.8 |
| 9 | 88.7 ± 18.2 |
| 10 (Na salt) | 110 ± 10 |
| 11 | 57 ± 11 |
| 14 | 75 ± 9 |

While the present invention has been illustrated above by certain specific embodiments, it is not intended that these specific examples should limit the scope of the invention as described in the appended claims.

We claim:

1. An (acyloxy) alkyl ester prodrug derivative of a 1H-indole-3-glyoxylamide of the invention represented by the formula (I);

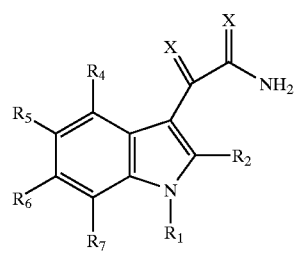

(I)

wherein;

both X are oxygen;

R$_1$ is selected from the group consisting of

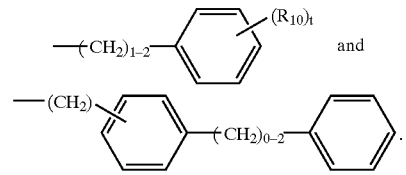

where R$_{10}$ is a radical independently selected from halo, C$_1$–C$_{10}$ alkyl, C$_1$–C$_{10}$ alkoxy, —S—(C$_1$–C$_{10}$ alkyl), and C$_1$–C$_{10}$ haloalkyl and t is a number from 0 to 5;

R$_2$ is selected from the group; halo, cyclopropyl, methyl, ethyl, and propyl;

R$_4$ and R$_5$ are independently selected from hydrogen, a non-interfering substituent, or the group, —(L$_a$)-(acidic group); wherein —(L$_a$)— is an acid linker; provided, the acid linker group, —(L$_a$L—, R$_4$ is selected from the group consisting of;

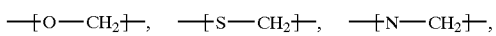

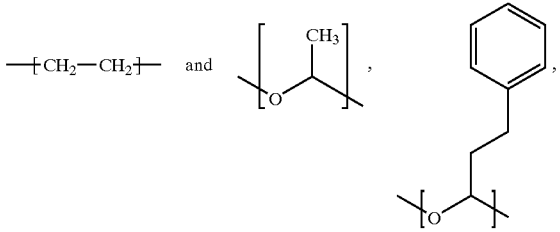

and provided, the acid linker, —(L$_a$)—, for R$_5$ is selected from group consisting of;

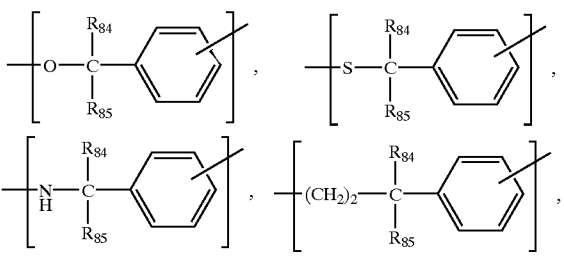

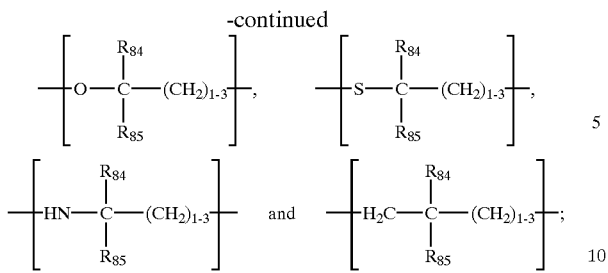

wherein $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo; and provided, that at least one of $R_4$ and $R_5$ must be the group, —($L_a$)-(acidic group) and wherein the (acidic group) on the group —($L_a$)-(acidic group) of $R_4$ or $R_5$ is selected from —$CO_2H$, —$SO_3H$, or —$P(O)(OH)_2$;

$R_6$ and $R_7$ are each independently selected form hydrogen and non-interfering substituents, with the non-interfering substituents being selected from the group consisting of the following: $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_2$–$C_{12}$ alkylamino, $C_1$–$C_6$ alkylthio, $C_2$–$C_2$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —$C(O)O(C_1$–$C_6$ alkyl), —$(CH_2)_n$—O—$(C_1$–$C_6$ alkyl), benzyloxy, phenoxy, phenylthio, —($CONHSO_2R$), —CHO), amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$–$C_6$ carbonyl; where n is from 1 to 8.

* * * * *